(12) United States Patent
Tal et al.

(10) Patent No.: US 9,180,039 B2
(45) Date of Patent: Nov. 10, 2015

(54) INTRAUTERINE DEVICE

(75) Inventors: Michael G. Tal, Savyon (IL); Patrick N. Gutelius, Monroe, CT (US); Mark J. DeBisschop, Harwinton, CT (US); Oleg Shikhman, Trumball, CT (US); Pasquale Patrizio, Guilford, CT (US); Bob H. Katz, San Jose, CA (US)

(73) Assignees: Yale University, New Haven, CT (US); ContraMed, LLC, Campbell, CA (US)

(*) Notice: Subject to any disclaimer, the term of this patent is extended or adjusted under 35 U.S.C. 154(b) by 598 days.

(21) Appl. No.: 13/294,091

(22) Filed: Nov. 10, 2011

(65) Prior Publication Data

US 2012/0097172 A1    Apr. 26, 2012

Related U.S. Application Data

(63) Continuation-in-part of application No. 12/856,876, filed on Aug. 16, 2010, now Pat. No. 8,662,081.

(51) Int. Cl.
*A61F 6/14* (2006.01)
*A61F 6/18* (2006.01)
*A61F 6/20* (2006.01)

(52) U.S. Cl.
CPC ............... *A61F 6/144* (2013.01); *A61F 6/142* (2013.01); *A61F 6/18* (2013.01); *A61F 6/20* (2013.01)

(58) Field of Classification Search
USPC .................. 128/830–840; 424/432
See application file for complete search history.

(56) References Cited

U.S. PATENT DOCUMENTS

| | | | |
|---|---|---|---|
| 3,374,788 A * | 3/1968 | Rosenthal | 128/840 |
| 3,391,844 A | 7/1968 | Vennard et al. | |
| 3,405,711 A | 10/1968 | Bakunin | |
| 3,507,274 A | 4/1970 | Soichet | |
| 3,620,212 A | 11/1971 | Fannon, Jr. et al. | |
| 3,659,596 A | 5/1972 | Robinson | |
| 3,678,927 A | 7/1972 | Soichet | |
| 3,683,905 A * | 8/1972 | Chaft | 128/839 |

(Continued)

FOREIGN PATENT DOCUMENTS

| | | |
|---|---|---|
| CH | 688984 | 7/1998 |
| DE | 4412311 | 10/1995 |

(Continued)

OTHER PUBLICATIONS

Valle, Tissue Response to the STOP Microcoil Transcervical Permane Contraceptive Device: Results from a Prehysterectomy Study, Fertility and Sterility, V.76, Iss. 5, Nov. 2001.

(Continued)

*Primary Examiner* — Ophelia A Hawthorne
(74) *Attorney, Agent, or Firm* — Welsh Flaxman & Gitler LLC

(57) ABSTRACT

An intrauterine device for applying force to a wall of a uterus to promote contraception without blocking the fallopian tubes may include an elongate member formed of a resilient material and having a default expanded configuration and a spring portion disposed approximately at a midpoint between two ends of the elongate member. The IUD may also include two tissue contact members, one tissue contact member disposed at one of the two ends of the elongate member and the other tissue contact member disposed at the other end. The tissue contact members may generate a laterally directed force against the wall of the uterus when the intrauterine device assumes its default expanded configuration.

17 Claims, 30 Drawing Sheets

(56) References Cited

U.S. PATENT DOCUMENTS

| | | | |
|---|---|---|---|
| 3,683,906 A | 8/1972 | Robinson | |
| 3,687,129 A | 8/1972 | Nuwayser | |
| 3,704,704 A | 12/1972 | Gonzales | |
| 3,716,052 A * | 2/1973 | Chaft | 128/839 |
| 3,789,838 A | 2/1974 | Fournier | |
| 3,805,767 A | 4/1974 | Erb | |
| 3,811,435 A | 5/1974 | Soichet | |
| 3,845,761 A | 11/1974 | Zaffaroni | |
| 3,881,475 A * | 5/1975 | Gordon et al. | 128/839 |
| 3,918,443 A | 11/1975 | Vennard et al. | |
| 4,034,749 A | 7/1977 | Von Kesseru et al. | |
| 4,117,839 A | 10/1978 | Morris | |
| 4,353,363 A | 10/1982 | Sopena Quesada | |
| 4,537,186 A | 8/1985 | Verschoof et al. | |
| 4,612,924 A | 9/1986 | Cimber | |
| 4,628,924 A | 12/1986 | Cimber | |
| 4,932,421 A | 6/1990 | Kaali et al. | |
| 5,095,917 A | 3/1992 | Vancaillie | |
| 5,146,931 A * | 9/1992 | Kurz | 128/833 |
| 5,555,896 A | 9/1996 | Cimber | |
| 5,935,137 A | 8/1999 | Saadat et al. | |
| 6,042,030 A | 3/2000 | Howe et al. | |
| 6,346,102 B1 | 2/2002 | Harrington et al. | |
| 6,705,323 B1 | 3/2004 | Nikolchex et al. | |
| 7,621,276 B2 | 11/2009 | Tal et al. | |
| 7,669,601 B2 | 3/2010 | Tal | |
| 8,181,653 B2 | 5/2012 | Tal et al. | |
| 8,662,081 B2 | 3/2014 | Tal et al. | |
| 9,016,280 B2 | 4/2015 | Tal et al. | |
| 2002/0198547 A1 | 12/2002 | Schultz | |
| 2003/0066533 A1 | 4/2003 | Loy | |
| 2004/0009205 A1 | 1/2004 | Sawhney | |
| 2005/0125022 A1 | 6/2005 | Ravikumar et al. | |
| 2005/0171569 A1 | 8/2005 | Girard et al. | |
| 2005/0192616 A1 | 9/2005 | Callister et al. | |
| 2008/0264423 A1 * | 10/2008 | Duchon et al. | 128/830 |
| 2008/0302368 A1 | 12/2008 | McGuckin et al. | |
| 2009/0178682 A1 | 7/2009 | Tal et al. | |

FOREIGN PATENT DOCUMENTS

| | | |
|---|---|---|
| EP | 0011143 | 5/1980 |
| EP | 0208653 | 1/1987 |
| FR | 2538243 | 6/1984 |
| IT | 1053357 | 8/1981 |
| JP | 59-214444 | 12/1984 |
| JP | 61-42914 | 3/1986 |
| WO | WO90/01310 | 2/1990 |
| WO | WO2006/088909 | 8/2006 |

OTHER PUBLICATIONS

Office Action, U.S. Appl. No. 13/949,621, May 5, 2015.

* cited by examiner

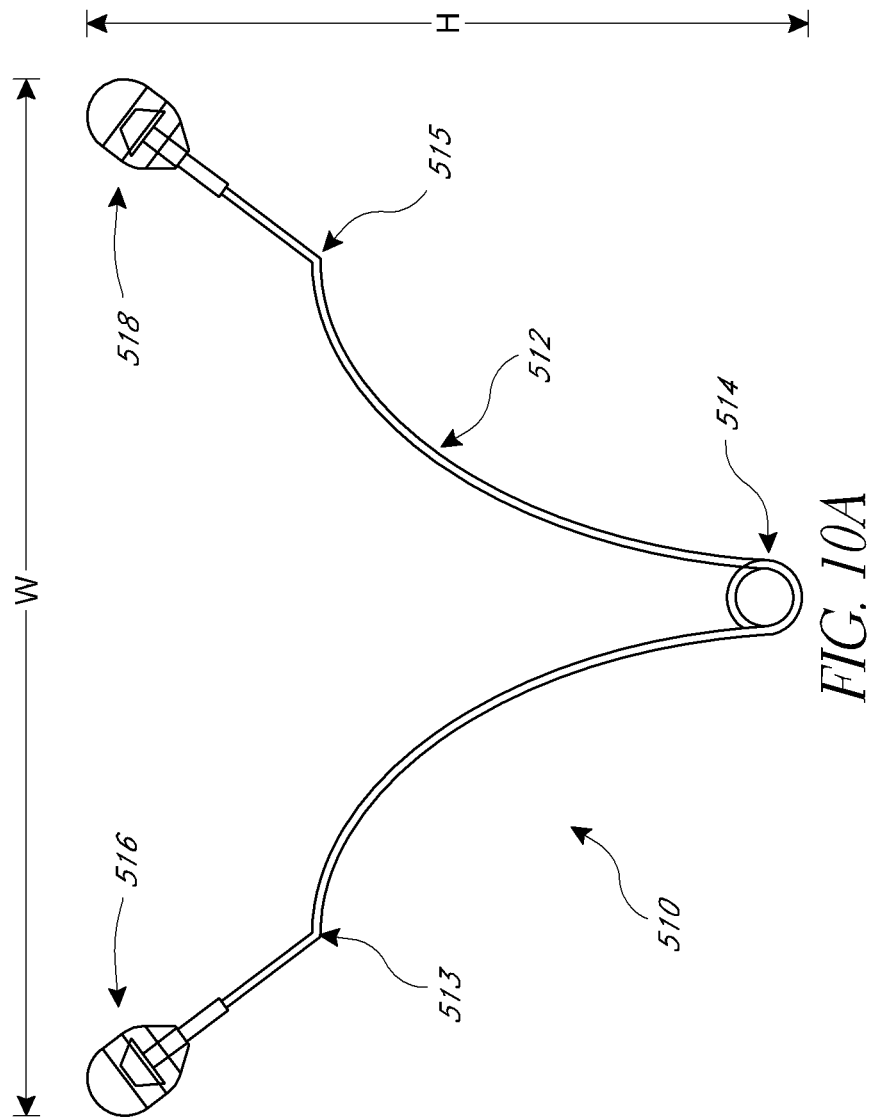

INTRAUTERINE DEVICE

CROSS-REFERENCE TO RELATED APPLICATIONS

This application is a continuation-in-part of U.S. patent application Ser. No. 12/856,876 (Pub. No. 2010/0300452), now U.S. Pat. No. 8,662,081 B2, entitled "Intrauterine Device" which was filed on Aug. 16, 2010, the full disclosure of which is hereby incorporated by reference.

BACKGROUND OF THE INVENTION

1. Field of the Invention

The invention relates generally to medical devices. More specifically, the invention relates to an intrauterine device and method for use.

2. Description of the Related Art

Intrauterine devices (IUDs) are a commonly used form of contraception. Generally, IUDs are believed to work by producing a spermicidal environment in the uterus and thus preventing fertilization of the egg by sperm. They may also have a post-fertilization effect, but IUDs are generally believed to produce all their contraceptive effects before implantation. In other words, IUDs are not believed to act as an abortifacient. They also typically do not affect ovulation.

There are two basic types of currently available IUDs. The copper IUD is a T-shaped device made of polyethylene wrapped with copper wire. The device acts as a foreign body within the uterus and releases copper to produce a chemical effect on the endometrium of the uterus and to alter the production of cervical mucus, thus producing a spermicidal environment. The copper IUD is approved by the FDA for ten years of continuous use.

Levonorgestrel (or "progesterone-releasing") IUDs are also T-shaped devices and include a sleeve containing levonorgestrel, which is released into the uterus over time. The levonorgestrel adds to the foreign body effects to create added spermicidal action and also thickens cervical mucus to act as a barrier to sperm penetration into the uterus. Levonorgestrel IUDs are approved by the FDA for five years of continuous use.

Although both copper and progestin-releasing IUDs work well for contraception, both have common side effects. The most common side effects with copper IUDs are abnormal bleeding and pain. The most common side effects with levonorgestrel IUDs are hormone-related effects, such as headaches, nausea, breast tenderness, depression and cyst formation. Although complications with IUDs are uncommon, there are cases of expulsion of the IUD from the uterus and failure of the device to work, either of which may result in unwanted pregnancy. Other possible complications are perforation of the uterine wall by the IUD or intrauterine infection.

Another type of implantable contraceptive device is designed for blocking the fallopian tubes to prevent conception. One example of such a device is the Essure® permanent birth control device, manufactured by Conceptus, Inc., Mountain View, Calif. (www.essure.com). The main drawback of fallopian tube blocking implants, however, is that they are typically permanent. These devices generally promote tissue in-growth (growth of tissue in/around the implant), which permanently attaches the implant to the fallopian tube wall. This works well for permanent contraception but makes removal of such devices difficult or even impossible. Another potential drawback of such devices is that they may be more difficult to place than IUDs that simply remain in the uterus. The openings to the fallopian tubes are small and located near the top of the uterus, so placing blocking implants into the fallopian tubes may be more challenging than simply placing a device in the uterus.

Therefore, although existing IUDs work relatively well for their purpose of contraception, there is still a need for improved IUDs. Ideally, such improved IUDs would be long-acting, have relatively few, minor side effects and potential complications, and be easy to deliver and remove. At least some of these objectives are met by the embodiments described in this application.

SUMMARY OF THE INVENTION

In one aspect of the present invention, a method is described for promoting contraception by applying force against an inner wall of a uterus without blocking the fallopian tubes. The method may involve advancing a distal end of a delivery device through a cervix, advancing an intrauterine device out of the distal end of the delivery device and into the uterus, and removing the delivery device. Advancing the intrauterine device out of the delivery device causes it to expand into an expanded configuration to cause two tissue contact members of the intrauterine device to move in approximately opposite directions to contact and apply force against the inner wall of the uterus. Each of the tissue contact members, when the intrauterine device is delivered, is positioned near, but not within, an opening of a fallopian tube. The two tissue contact members apply sufficient force against the uterine wall to promote contraception and prevent migration of the intrauterine device out of the uterus or into the fallopian tubes.

In some embodiments, each of the tissue contact members, when the device is delivered, is positioned within 2 cm of a fallopian tube opening. Also in some embodiments, the tissue contact members, when the intrauterine device is delivered into the uterus and expands to its expanded configuration, generate a total, laterally directed force against the inner wall of the uterus of between about 0.002 pounds-force and about 0.025 pounds-force, and ideally between about 0.002 pounds-force and about 0.015 pounds-force.

In some embodiments, the method may further involve causing a disruption or collapse of the uterine spiral arteries using the tissue contact members. Some embodiments may optionally further involve causing a localized ischemia to endometrial tissue of the uterus using the tissue contact members. The method may also involve preventing tissue in-growth, uterine wall perforation, and migration of the tissue contact members by providing the tissue contact members with a material, size and shape that resist in-growth, perforation and migration.

In one embodiment, the method may further include removing the intrauterine device from the uterus through the cervix. For example, in one embodiment, removing the intrauterine device may involve pulling on a thread connected to the intrauterine device.

In some embodiments, advancing the intrauterine device out of the delivery device comprises moving at least one of a sheath and a pusher member of the delivery device relative to one another. In various embodiments, the sheath may be held steady and the pusher may be advanced, the pusher may be held steady and the sheath may be retracted, or the pusher may be advanced while the sheath is retracted.

In many embodiments, the intrauterine device does not deliver a chemical substance to the uterus. In some embodiments, however, the method may further include delivering a substance to the uterus via the tissue contact members. Such a substance may include, for example, one or more hormones, spermicides, copper or therapeutic agents.

In another aspect of the present invention, a method for promoting contraception by applying force against a wall of a uterus without blocking the fallopian tubes may include applying constant force against approximately opposed sides of an inner wall of the uterus with a removable intrauterine device having at least two tissue contact members disposed at opposite ends of an elongate, resilient member that expands from a compressed configuration into a default, expanded configuration to cause the tissue contact members to apply the force against the wall of the uterus at locations near but not within the fallopian tubes. Applying the force may involve placing the intrauterine device into the uterus through the cervix using a delivery device.

In another aspect, a method of promoting contraception without blocking the fallopian tubes may include expanding a uterine cavity by an amount sufficient to promote contraception. In some embodiments, the expanding involves placing an expandable device in the uterine cavity. In most embodiments, the device is essentially free of copper and hormones, while in alternative embodiments it may include one or more hormones, copper or therapeutic agents.

In another aspect of the present invention, an intrauterine device for applying force to a wall of a uterus to promote contraception without blocking the fallopian tubes may include an elongate member and two tissue contact members. The elongate member may be formed of Nitinol, may have a diameter between about 0.010 inch and about 0.025 inch, and may have a default expanded configuration and a spring portion disposed approximately at a midpoint between two ends of the elongate member. One tissue contact member is disposed at one end of the elongate member, and the other tissue contact member is disposed at the other end. In some embodiments, each tissue contact member is made of a non-porous material and has a surface area of at least about 30 mm squared. Also in some embodiments, the intrauterine device has a width measured from a tip of one tissue contact member to a tip of the other tissue contact member of at least about 40 mm in its expanded configuration outside the uterus.

In some embodiments, the tissue contact members generate a total, laterally directed force against the wall of the uterus of between about 0.002 pounds-force and about 0.025 pounds-force, and even more ideally between about 0.002 pounds-force and about 0.015 pounds-force, when the intrauterine device assumes its default expanded configuration within the uterus.

The spring portion may have any of a number of different configurations, although in one embodiment it comprises a spring having at least one coil formed in the elongate member. In some embodiments, the default expanded configuration of the elongate member comprises a V-shape, with the spring portion disposed at a vertex of the V-shape, and where the elongate member curves laterally from the spring portion to each of the two ends. In some embodiments, a height of the device measured from a bottom of the spring portion to a top of the tissue contact members is at least about 25 mm. Optionally, the elongate member may further include at least two bends configured to reduce the amount of laterally directed force, one bend disposed between the spring portion and one of the two ends, and the other bend disposed between the spring portion and the other end.

In some embodiments, the intrauterine device may be compressible into a collapsed configuration for positioning within a delivery sheath having an inner diameter of no more than about 3.9 mm. Also in some embodiments, the elongate member may have a diameter of between about 0.014 inch and about 0.015 inch.

The device may optionally further include at least one additional tissue contact member for contacting the uterine wall at a different location. For example, the additional tissue contact member may include at least one fundus contact member coupled with at least one of the two tissue contact members via an additional Nitinol elongate member for contacting a fundus of the uterus.

In some embodiments, the device may further include a substance disposed in a hollow channel in the elongate member or in or on the tissue contact members. For example, the substance may include but is not limited to one or more hormones, spermicides, copper or therapeutic agents.

In another aspect, a system for promoting contraception without blocking the fallopian tubes may include an elongate, at least partially hollow delivery device having an outer diameter suitable for passing through a cervix and an intrauterine device preloaded into the delivery device. The intrauterine device and the method for use may be similar to, or the same as, those described above. In some embodiments, the system may further comprise a substance for delivering to the uterus through the intrauterine device.

These and other aspects and embodiments of the invention are described in greater detail below, with reference to the drawing figures.

BRIEF DESCRIPTION OF THE DRAWINGS

FIG. 10A is a front view of an intrauterine device (IUD) having bends in an elongate member thereof, according to another alternative embodiment;

DETAILED DESCRIPTION OF THE PREFERRED EMBODIMENT

Figure 1:
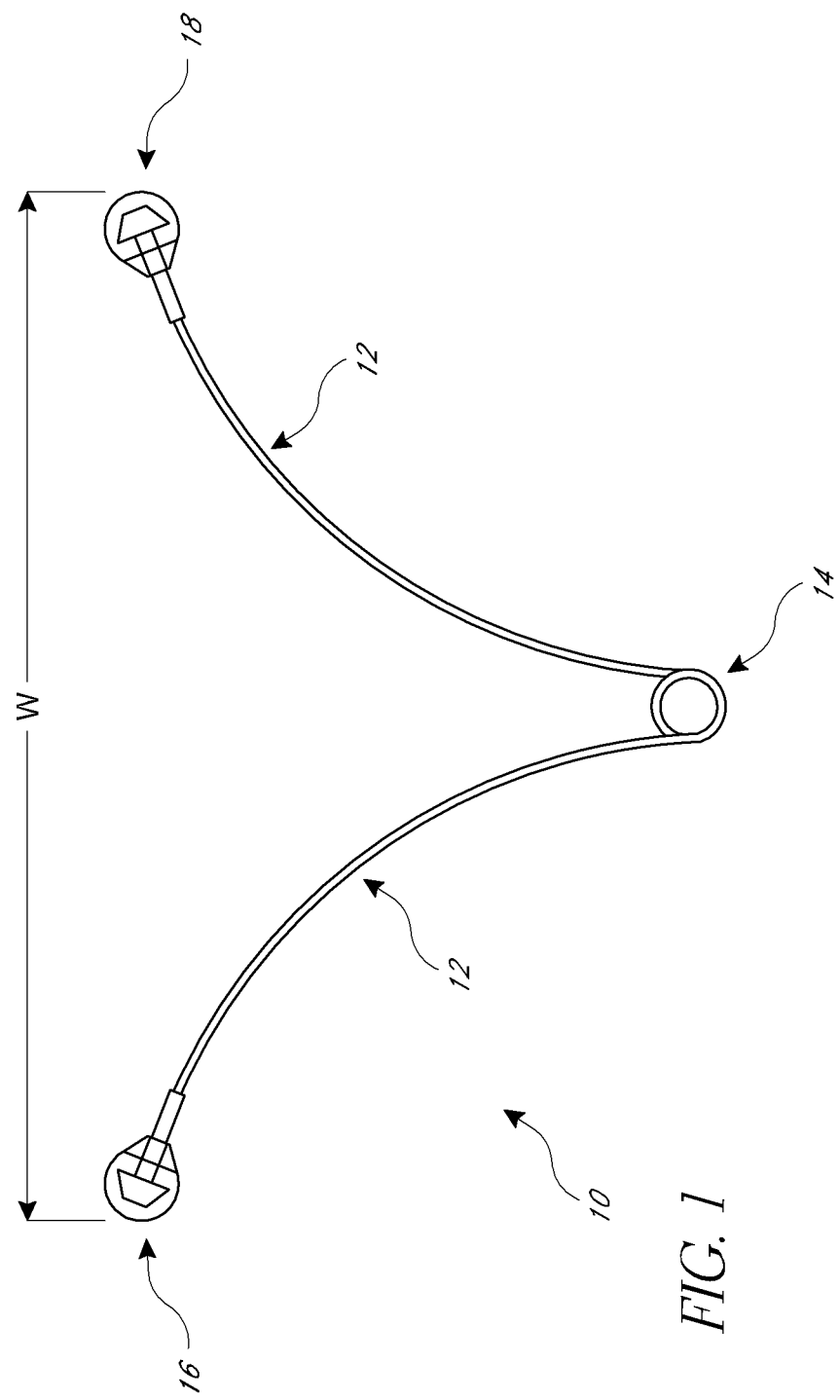
FIG. 1 is a front view of an intrauterine device (IUD), according to one embodiment.

Referring to FIG. 1, in one embodiment, an intrauterine device (IUD) 10 may include a resilient, elongate member 12 and two tissue contact members 16, 18 disposed at opposite ends of elongate member 12. Elongate member 12 may include a spring portion 14, typically disposed approximately at a midpoint between the opposite ends of elongate member 12. Elongate member 12 is manufactured from a resilient material, such as but not limited to Nitinol (nickel titanium alloy), and has a default (or "predetermined") expanded configuration as shown in FIG. 1. Elongate member 12 may be compressed into a low profile, collapsed configuration, to facilitate delivery of IUD 10 through a cervix, typically using a delivery device. When released from compression within the uterus, IUD 10 springs back into its default expanded configuration to allow tissue contact members 16, 18 to contact and apply force against the uterine wall.

As illustrated in FIG. 1, in one embodiment, IUD 10 has a generally V-shaped predetermined, expanded configuration. Spring portion 14 is disposed at the vertex of the V, and elongate body 12 has a slight outward curve between spring portion 14 and each tissue contact member 16, 18. Although this V-shaped configuration is described in reference to this embodiment, IUD 10 may have any of a number of different expanded configurations in alternative embodiments, examples of which are described further below. Furthermore, although the term "spring portion" is used to describe a portion of elongate member 12 that helps confer laterally directed force to tissue contact members 16, 18, spring portion 14 is not necessarily a spring. As will be described further below in reference to several examples, spring portion 14 may have any of a number of different shapes in alternative embodiments.

IUD 10 may be said to have a wingspan (or "width") W, as measured from a tip of one tissue contact member 16 to a tip of the other tissue contact member 18. IUD 10 may also be said to have a height (or "length") H, as measured from the bottom of spring portion 14 to the tops of tissue contact members 16, 18. Wingspan W and height H are generally selected to provide IUD 10 with a desired amount of laterally directed force at tissue contact members 16, 18, so that IUD 10 will maintain itself in a given location within the uterus and exert sufficient force to promote contraception. In one embodiment, for example, IUD 10 may have a height H of between about 25 mm and about 28 mm and a wingspan W of between about 44 mm and about 46 mm. Alternative sizes may be provided to enhance the effectiveness of IUD 10 in different female anatomies, but because IUD 10 is sufficiently resilient and the uterus is typically a closed space, IUD 10 is generally a "one size fits all" device.

As just mentioned, the uterus (or "uterine cavity") is generally not an open space. Even though the uterus is typically illustrated as an open space, such as in FIGS. 2A-2F, this is simply a schematic illustration, because the uterus itself is a closed space. IUD 10 should, therefore, have sufficient laterally directed force when released from a delivery device within the uterus to expand within the closed uterine cavity. The uterus is also typically a moist environment, so IUD 10 should have sufficient resiliency to overcome any surface tension that might hold the opposed surfaces of the inner wall of the uterus together. It is also important, of course, that IUD 10 apply sufficient laterally directed force to promote contraception. Prior to the present invention, IUD devices have been manufactured with attached or impregnated chemicals that elute into the uterus from the device to produce the spermicidal contraceptive properties. As noted above, these chemicals are also a major source of adverse side effects associated with these devices. Although devices in accordance with embodiments of the present invention may include such eluting chemicals, they are surprisingly not necessary for the device to be effective as a contraceptive. It is believed that force applied to the inner uterine wall by tissue contact members 16, 18 may by itself disrupt the uterine environment in such a way to cause a spermicidal effect, thus preventing conception. This effect has never before been observed, nor used to provide contraception prior to the present invention. The force exerted against the wall by IUD 10 may cause an inflammatory response, ischemia, compression of the spiral artery and/or a combination thereof, and any or all of these may help promote contraception. Finally, IUD 10 should have sufficient laterally directed force to prevent migration of the device to other parts of the uterus or expulsion of the device from the uterus. As is described in greater detail below, IUD 10 likely has the greatest contraceptive effect when delivered and maintained in a certain portion of the uterus, so ideally IUD 10 will have sufficient outwardly directed force to prevent device migration or expulsion. At the same time, another objective of IUD 10 is to prevent perforation of the uterine wall, so IUD 10 should not have an excessive amount of outwardly directed force. Each embodiment of IUD 10 described below is configured to provide an amount of laterally directed force to a uterine wall to achieve these objectives.

IUD 10 generates laterally directed, expansile force due to its resilient material (typically Nitinol), the diameter of its resilient material, and its default, expanded shape and size, including spring portion 14. Spring portion 14 may in some embodiments be an actual spring or looped portion of elongate member 12, while in alternative embodiments it may be any of a number of other suitable shapes that help confer laterally directed force to elongate member 12. This laterally directed force pushes tissue contact members 16, 18 against the uterine wall with sufficient force that they first move along the wall to a desired location for promoting contraception and then maintain their position on (or "adhere to") the wall at that location. IUD 10 may also have a shape, size, lateral force, and size and shape of tissue contact members 16, 18 that help prevent tissue contact members 16, 18 from advancing (or "migrating") into the fallopian tubes. It may be advantageous for IUD 10 to avoid entering the fallopian tubes, because this may facilitate removal of IUD 10 when desired. Delivery, adherence to the uterine wall and other characteristics of IUD 10 are described in further detail below. By generating adhering force against the uterine wall, IUD 10 remains in the uterus as a foreign body and provides further contraceptive effect by the application of force, thus preventing unwanted pregnancy safely and without the need for copper or progestin.

As mentioned, in one embodiment, elongate body 12 is made of Nitinol. In various embodiments, the diameter of elongate body 12 may be selected to help provide a desired amount of lateral force generation when the device is in the default expanded configuration of FIG. 1. For example, in some embodiments, elongate body 12 may be a Nitinol wire with a diameter of between about 0.010" and about 0.025" and more ideally between about 0.014" and about 0.015". Various diameters and configurations of elongate body 12 are described further along with their force generating properties.

In alternative embodiments, resilient materials other than Nitinol may be used, such as spring stainless steel. Nitinol is typically preferred, however, due to its ability to remain in a compressed configuration (such as in a delivery catheter) for long periods of time, fully spring back into its expanded configuration, and maintain a constant but gentle force against the uterine wall for many years of useful life of IUD 10. The material properties of a Nitinol IUD 10 allow it to be compressed into a collapsed or low profile configuration for storage in a delivery device, stored in that configuration for long periods of time, and then delivered out of the delivery device to assume its default, expanded configuration. Other resilient materials typically do not retain their full resilient properties over time in this way, although to the extent other materials would serve this purpose they may be used in alternative embodiments. Storing and/or packaging IUD 10 within a delivery device makes its use easier, because the end user (typically a physician or physician's assistant) is not required to load the device into the delivery device. IUD 10 formed of Nitinol is also unique in that it provides a constant lateral force in various uterine sizes and is thus a "one size fits all" device. Constant gentle lateral force along the inner uterine wall also prevents expulsion of IUD 10 out of the uterus, which is one of the potential complications of currently available IUDs.

Tissue contact members 16, 18 may be comprised of any of a number of suitable materials and may have a number of different sizes and shapes. Generally, the material, size and shape of tissue contact members 16, 18 are selected to prevent, or at least reduce the tendency for, tissue in-growth of tissue contact members 16, 18 into uterine wall tissue while also preventing migration or expulsion of IUD 10. Tissue in-growth prevention is important for facilitating later removal of IUD 10 from the uterus if and when desired. This prevention of tissue in-growth is in direct contrast to a number of prior art permanent contraception or sterilization devices that purposely try to promote tissue in-growth, for example to permanently attach a device within the fallopian tubes. IUD 10, in contrast, is usually easily removed and does not permanently adhere to the uterine wall. In one embodiment, tissue contact members 16, 18 may be made of a high density polyethylene. In alternative embodiments, tissue contact members 16, 18 may be made of any of a number of alternative, typically non-porous materials, such as but not limited to metals, plastics, elastomers such as silicone, or combinations thereof. Furthermore, tissue contact members 16, 18 may be coated, such as with a coating to prevent tissue in-growth, or may be impregnated with various medications or other substances, such as but not limited to hormone, spermicide or the like. Tissue contact members 16, 18 may also be made of (or coated with) an echogenic material to facilitate visualization of IUD 10 using transvaginal ultrasound or other visualization techniques.

Tissue contact members 16, 18 may have any suitable size and shape but are generally configured to apply a desired amount of force to the uterine wall to promote contraception, to maintain the position of IUD 10, and to prevent tissue in-growth, without causing pain or uterine wall perforation, a well known risk of currently available intrauterine devices. Tissue contact members 16, 18 must also be sized so that they can be effectively delivered through a low profile delivery device without pain to the patient. To achieve these goals, tissue contact members 16, 18 according to one embodiment have a diameter of between about 1 mm and about 8 mm, and preferably between about 2 mm and about 4 mm, and even more preferably between about 2.5 mm and about 3.5 mm. Tissue contact members 16, 18 according to this embodiment may have a length of between about 3.0 mm and about 5.0 mm, and preferably between about 3.5 mm and about 3.6 mm. Also according to one embodiment, each tissue contact member 16, 18 has a surface area of between about 30 mm squared and about 45 mm squared, and preferably between about 31 mm squared and about 32 mm squared. Providing tissue contact members 16, 18 with a relatively large surface area (while keeping them small enough to fit within a delivery device) may help prevent uterine wall perforation and in-growth, while still allowing for the application of a desired amount of laterally directed force against the uterine wall.

Various embodiments and features of IUD 10, elongate member 12, spring portion 14 and tissue contact member 16, 18 are described further below in reference to additional drawing figures.

Figure 2A:
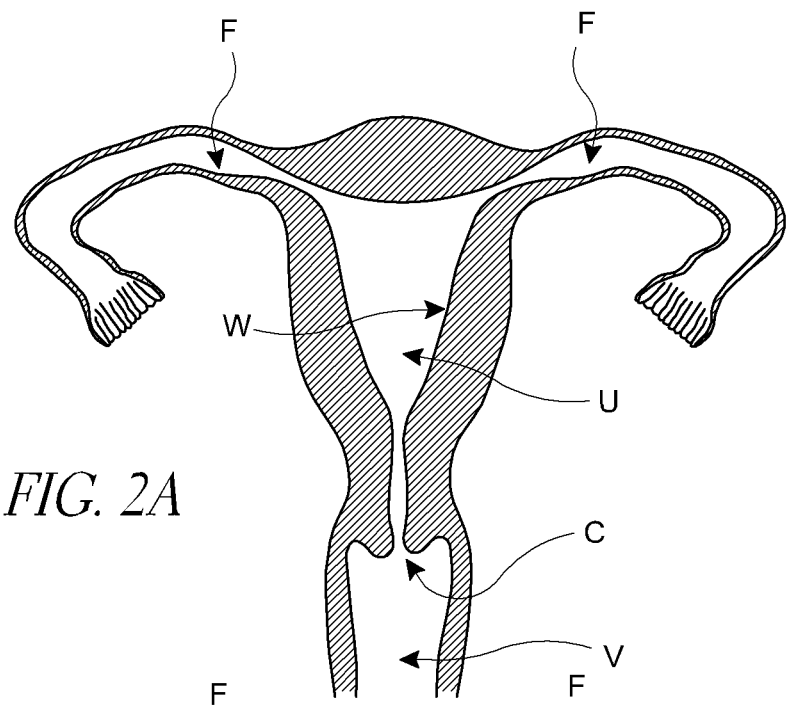
FIGS. 2A-2F show a cross-sectional view of a uterus, cervix and fallopian tubes, illustrating a method for delivering an intrauterine device (IUD) into a uterus, according to one embodiment.

Referring now to FIGS. 2A-2F, a portion of the female reproductive anatomy is shown in schematic form in cross-section, and a method for delivering IUD 10 to a uterus U is illustrated. As shown in FIG. 2A, the vagina V leads into the cervix C, which in turn leads into the uterus U (illustrated schematically as an open cavity). The uterus U has an inner wall W, which in this application is referred to simply as the uterine wall. Two fallopian tubes F branch off of the uterus U. During the natural reproductive cycle, eggs travel down the fallopian tubes F to be fertilized by sperm (typically within a fallopian tube F), and the fertilized egg then implants on the uterine wall W to grow into a fetus. IUD 10 works primarily or exclusively by producing a "hostile environment" in the uterus U for sperm and thus preventing fertilization, or secondarily, if fertilization occurs, by blocking implantation.

Figure 2B:
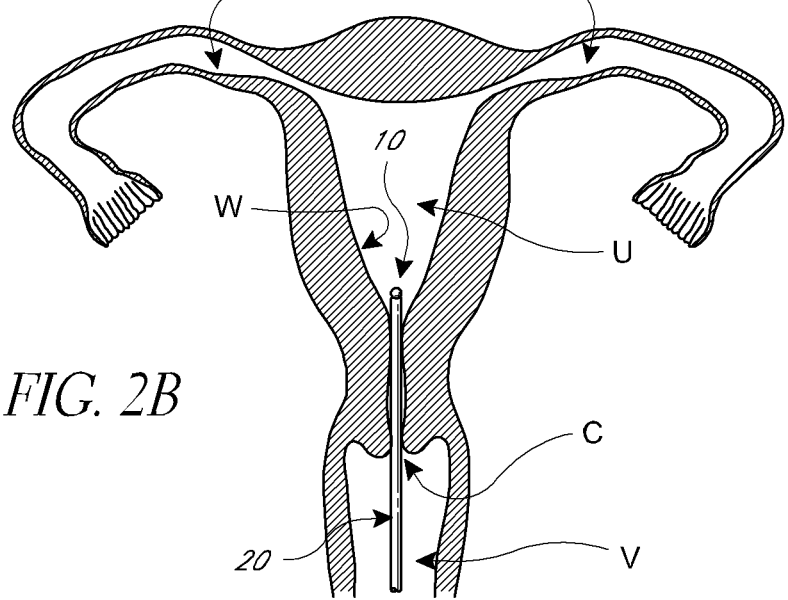

With reference to FIG. 2B, as a first step in a method for IUD delivery, an IUD delivery device 20 containing IUD 10 may be advanced through the cervix C into the uterus U. While housed in delivery device 20, IUD 10 is in a collapsed, low profile configuration to facilitate its passage through the cervix C. In some embodiments, a distal portion of IUD 10 may protrude from a distal end of delivery device 20 during delivery, as shown. Alternatively, IUD 10 may be completely contained within delivery device 20. Delivery device 20 may take any of a number of suitable forms, typically including an outer sheath (or catheter or tubular member) and an inner pusher member, as described further below.

Figure 2C:
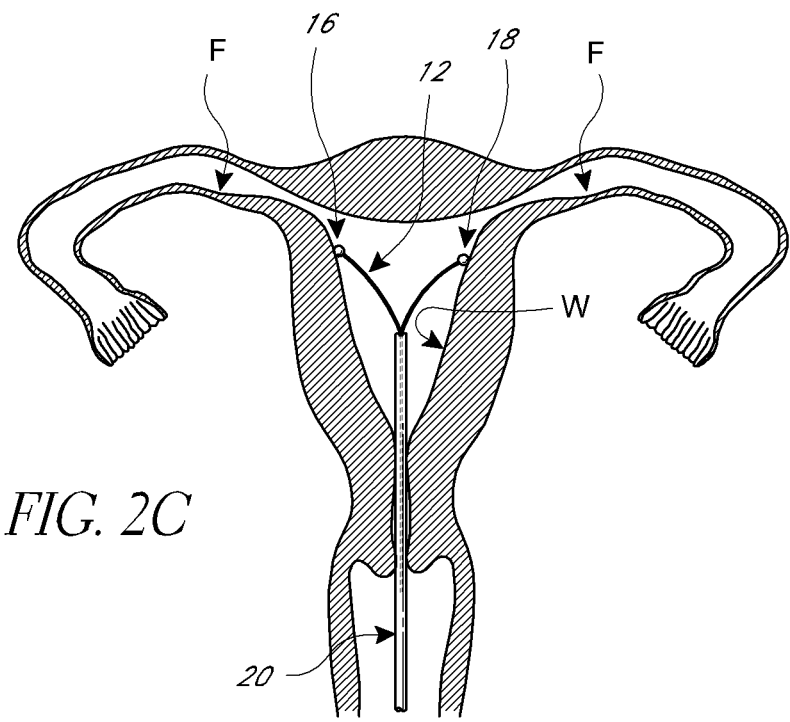

FIG. 2C shows the next step in the delivery process according to one embodiment, with IUD 10 partially expelled from delivery device 20 into the uterus U. At this point, tissue contact members 16, 18 are contacting the uterine wall W. In various embodiments, IUD 10 may be expelled from delivery device 20 using any of a number of different techniques and mechanisms. In one embodiment, for example, a pusher member in delivery device 20 may be held in a stable position, and a sheath on delivery device 20 may be retracted to expose IUD 10. Alternatively, a sheath may be held in a stable position and a pusher member may be advanced to push IUD 10 out of the distal end of delivery device 20. In another embodiment, a pusher member may be advanced while a sheath is retracted. In other alternative embodiments, other suitable means for expelling IUD 10 from delivery device 20 may be used.

Figure 2D:
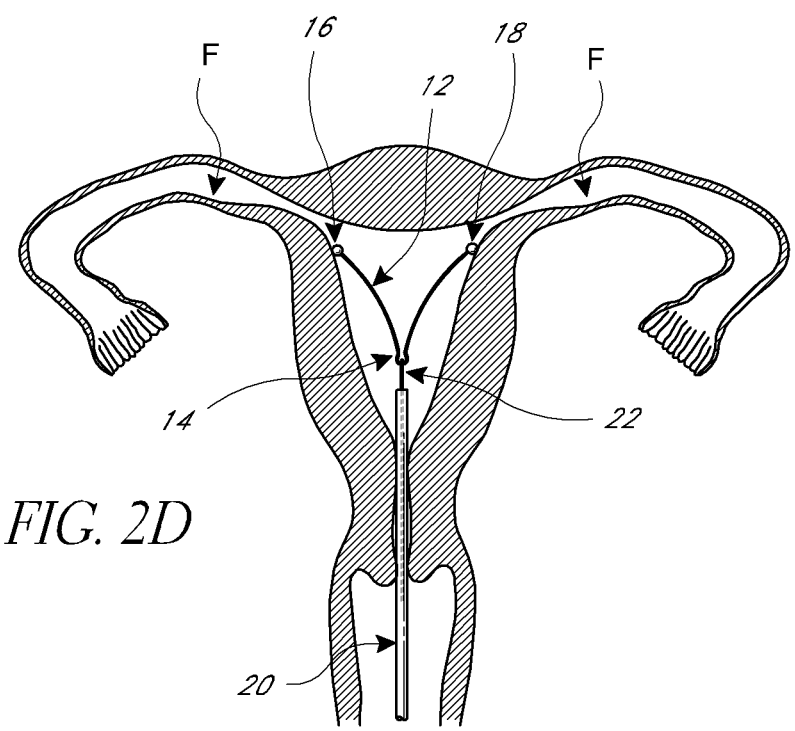

In FIG. 2D, IUD 10 has been completely expelled from delivery device 20 but is still in contact with a pusher member 22 of delivery device. Comparing the position of IUD 10 in FIGS. 2C and 2D shows that IUD 10 may advance along the uterine wall W toward the fallopian tubes F during and/or after delivery to eventually seat (or "adhere") in an area just inferior of the fallopian tube openings. Alternatively, IUD 10 may simply be delivered directly to the desired location within the uterus U rather than delivering it to an initial location and having it ride along the uterine wall W before seating at its final location. The words "seat" and "adhere" do not mean that IUD 10 permanently attaches to the uterine wall. In fact, as previously mentioned, tissue contact members 16, 18 and IUD 10 are designed to prevent tissue ingrowth and permanent attachment to the uterine wall. "Seating" and "adhering" are thus generally used to simply mean maintaining a relative position along the uterine wall. Ideally, but not necessarily, each tissue contact member 16, 18 will seat in an area of the uterine wall W within approximately 2 cm inferior of a fallopian tube opening, and preferably within approximately 1 cm inferior of a fallopian tube opening. This is believed to be an ideal area for IUD 10 to reside for contraception, although an exact location for IUD 10 within the uterus is not required.

Movement of IUD 10 along the uterine wall and adherence of IUD 10 at a given location are caused by a combination of the amount of outward force produced inherently by IUD 10, the size and shape of IUD 10, the size, shape and physical characteristics of tissue contact members 16, 18, and the size and shape of the uterus U. IUD 10 is configured to have enough outwardly directed force and other characteristics to make IUD 10 adhere to the uterine wall W, typically near the fallopian tube orifices, without actually entering the fallopian tubes F. The force applied to the uterine wall W by the IUD 10 is believed to be at least one reason that IUD 10 prevents pregnancy. The constant, gentle force applied to the uterine wall W is believed to disrupt the natural uterine environment.

In its fully expanded, default configuration, IUD 10 assumes its V-shape with curved elongate member 12 portions between spring portion 14 and tissue contact members 16, 18. In various embodiments, IUD 10 may have a wingspan (described previously), when fully expanded in the uterus U, of between about 18 mm and about 54 mm, depending upon the anatomical characteristics of the patient. The wingspan of IUD 10 may be selected at least in part due to the distance between the uterine wall W just inferior to one fallopian tube F and the uterine wall W just inferior to the opposite fallopian tube F. For example, the average intra-ostial distance in nulliparous women is 29.2 mm, and the average intra-ostial distance in parous women is 30.0 mm, so the IUD wingspan may in some embodiments be based at least in part on these measurements. "Assessment Of The Uterine Cavity And The Intraostial Distance Using Hysterosalpingography", Fertility and Sterility, Volume 88, Supplement 1, September 2007, Page S202, J. G. Bromer, F. Sanguinetti, M. Tal, P. Patrizio. Obstetrics, Gynecology, and Reproductive Sciences, Yale University School of Medicine, New Haven, Conn.; Department of Radiology, Yale University School of Medicine, New Haven, Conn.

As described previously, when expanded, IUD 10 applies laterally directed force against the uterine wall W via tissue contact members 16, 18 to cause irritation/inflammation, ischemia, compression of arterial structures, and/or other effects that promote contraception. Additionally, IUD 10 may apply sufficient force to slightly distort the shape of the uterine wall W, which is believed to further promote contraception. The amount of laterally directed force applied to the uterine wall W, both for adherence of IUD 10 (and thus migration and expulsion prevention), as well as for the added effect of uterine wall distortion, is important for proper functioning of the device. In various embodiments, a range of the force applied by tissue contact members 16, 18 to the uterine wall is between about 0.002 pounds-force and about 0.025 pounds-force, and ideally between about 0.002 pounds-force and about 0.015 pounds-force.

Figure 2E:
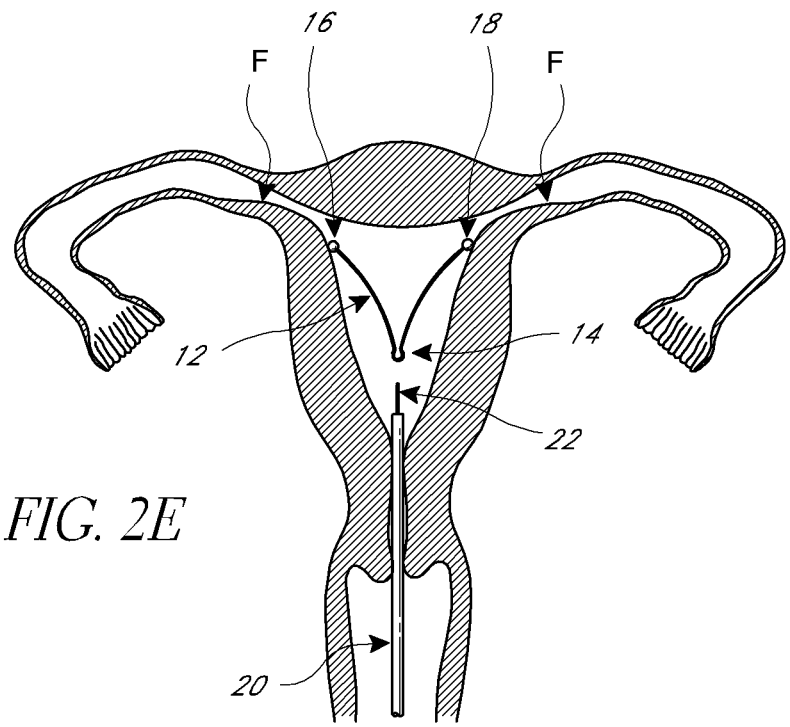
Figure 2F:
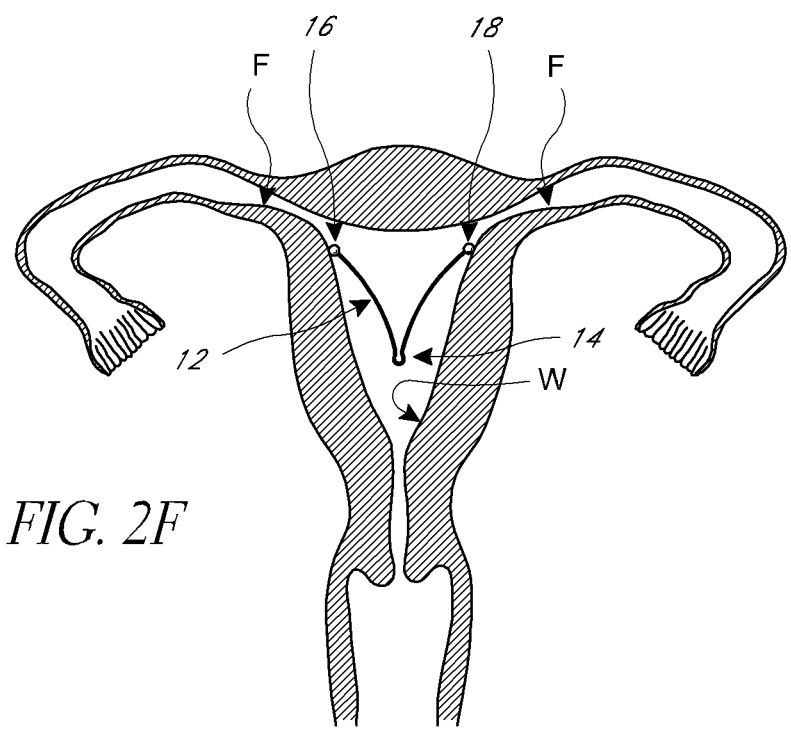

Referring to FIG. 2E, IUD 10 is shown in place in the uterus U, completely disconnected from delivery device 20. At this point, delivery device 20 may be removed through the cervix C, leaving IUD 10 in place, as shown in FIG. 2F. IUD 10 then remains in the uterus U for as long as desired to promote contraception.

IUD 10 may be left in the uterus U permanently or may be removed at any time. Because IUD 10 is easily delivered and removed, it allows for nonsurgical contraception as an office procedure and without the need for surgery or the necessity for visualization either radiologically, ultrasonically, or with a hysteroscope. IUD 10 uses radial force and inherent properties in its construction to promote contraception, thus eliminating the need for hormones or copper in the device. IUD 10 also uses radial force prevent migration or expulsion of the intrauterine device 10. As such, IUD 10 may be used for permanent or temporary contraception. As described further below, although IUD 10 does not require the use of hormones, copper or other substances, in some embodiments it may also be adapted for local delivery of these or other therapeutic agents. Therefore, IUD 10 may be used, in some embodiments, not only for contraception but also for treatment of one or more conditions such as abnormal uterine bleeding and/or pelvic pain.

Figure 3A:
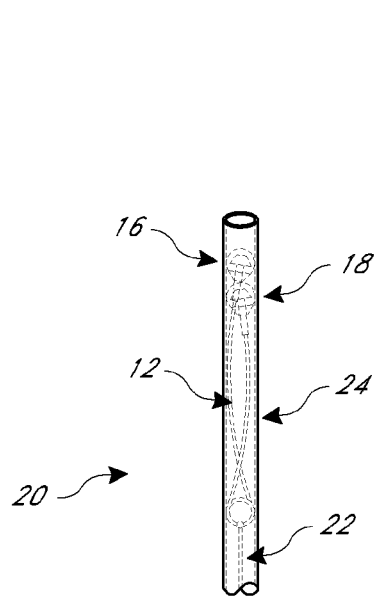
FIGS. 3A-3D are perspective views of an IUD and a distal portion of an IUD delivery device, illustrating a method for delivering the IUD out of the delivery device, according to one embodiment.

Referring now to FIGS. 3A-3D, IUD 10 and a distal portion of delivery device 20 are shown, illustrating one embodiment of delivery device 20 and a method for delivering IUD 10 out of delivery device 20 in greater detail. Delivery device 20 is relatively simple to use, does not require intrauterine visualization by the physician, and has a small diameter to allow insertion without pre dilatation, pain or use of local anesthesia. In the embodiment shown, delivery device 20 includes a sheath 24 and pusher member 22. As shown in FIG. 3A, IUD 10 may be housed completely within delivery device 20 for packaging and/or delivery of IUD 10 through the cervix. To fit both tissue contact members 16, 18 within a low profile sheath 24, tissue contact members 16, 18 may be staggered longitudinally relative to one another, as illustrated in FIG. 3A. This may be achieved by having a portion of elongate member 12 bow out slightly, so that one tissue contact member 16 can tuck in behind the other tissue contact member 18. In an alternative embodiment, a portion of elongate member 12 between spring portion 14 and one tissue contact member 16 may be longer than another portion of elongate member 12 between spring portion 14 and the other tissue contact member 18. In another alternative embodiment, tissue contact members 16, 18 may be aligned side by side within sheath 24 and may simply have a size, shape and/or material that allow them to fit within sheath 24 in that configuration.

Sheath 24 may have an outer diameter sized to allow it to pass painlessly or relatively painlessly through a cervix. In some embodiments, for example, sheath 24 has an outer diameter of no more than 5.0 mm and ideally no more than 4.5 mm. According to some embodiments, sheath 24 may have an inner diameter of no more than about 4.9 mm and ideally no more than about 3.9 mm. IUD 10 is compressible into a compressed configuration having a diameter to fit within the inner diameter of sheath 24. Sheath 24 may be made of a flexible polymeric material in one embodiment, but in alternative embodiments it may be rigid and/or made of other materials, such as metal. In some embodiments, sheath 24 may be coated with a lubricious coating to facilitate passage through the cervix.

Figure 3B:
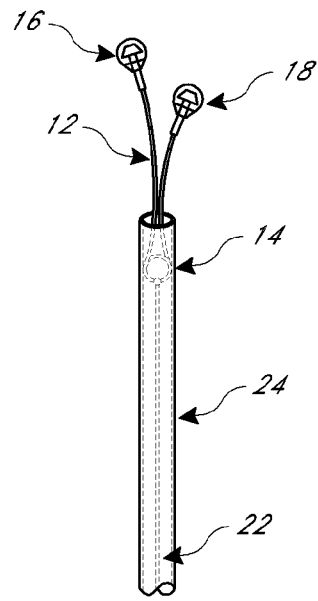

In FIG. 3B, pusher member 22 has been advanced to push IUD 10 partially out of the distal end of sheath 24. In various embodiments, pusher member 22 may be advanced while sheath 24 is held relatively stable, pusher member 22 may be held relatively stable while sheath 24 is retracted, or pusher member 22 may be advanced while sheath 24 is retracted.

Figure 3C:
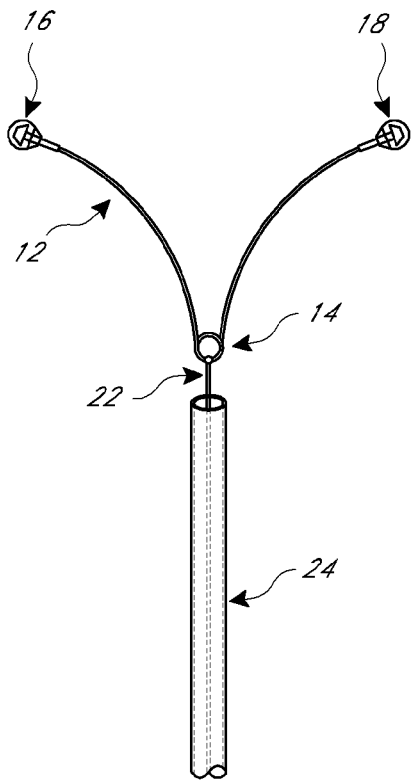
Figure 3D:
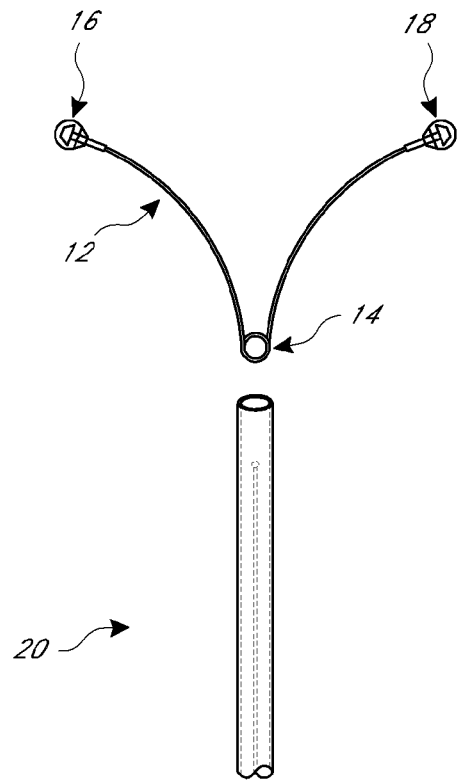

In FIG. 3C, pusher member 22 has advanced IUD 10 completely out of sheath 24, and IUD 10 has sprung into its default, expanded configuration. In FIG. 3D, pusher member 22 has been retracted back into sheath 24. Both pusher member 22 and sheath 24 may be made of any suitable, biocompatible material, such as a metal and/or a polymer. Typically, though not necessarily, delivery device 20 will be disposable. Alternatively, it may be reusable, in which case it will be made of material(s) that allow for re-sterilization.

Figure 4A:
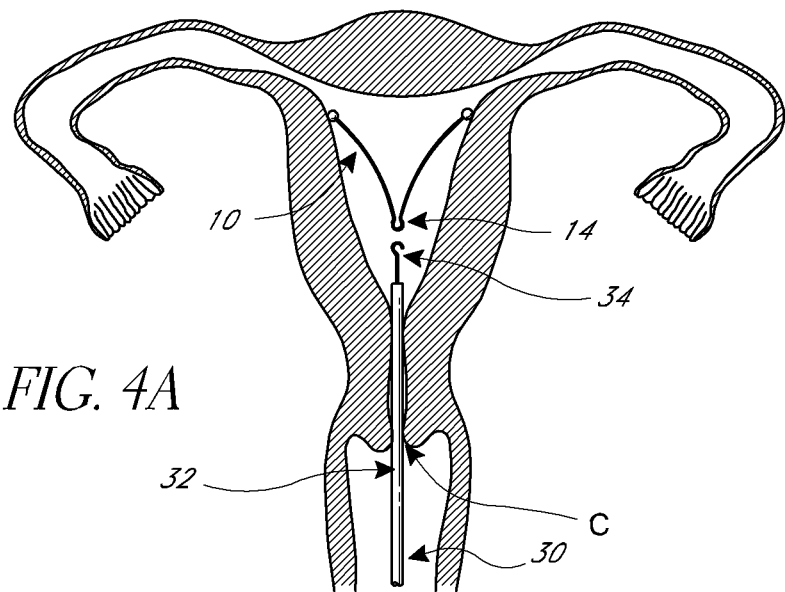
FIGS. 4A-4F show a cross-sectional view of a uterus, cervix and fallopian tubes, illustrating a method for retrieving an IUD from a uterus, according to one embodiment.

FIGS. 4A-4F illustrate a method for removing IUD 10 from a uterus U. FIG. 4A shows IUD 10 in place in the uterus U and a removal device 30 advanced into the uterus U through the cervix C. In the embodiment shown, removal device 30 includes a sheath 32 and a removal member having a hook 34 at its distal end. Hook 34 is configured to couple with IUD 10 to pull it out through sheath 32. In alternative embodiments, any suitable attachment device may be used instead of a hook, such as a clasp, forceps, clip or the like.

Figure 4B:
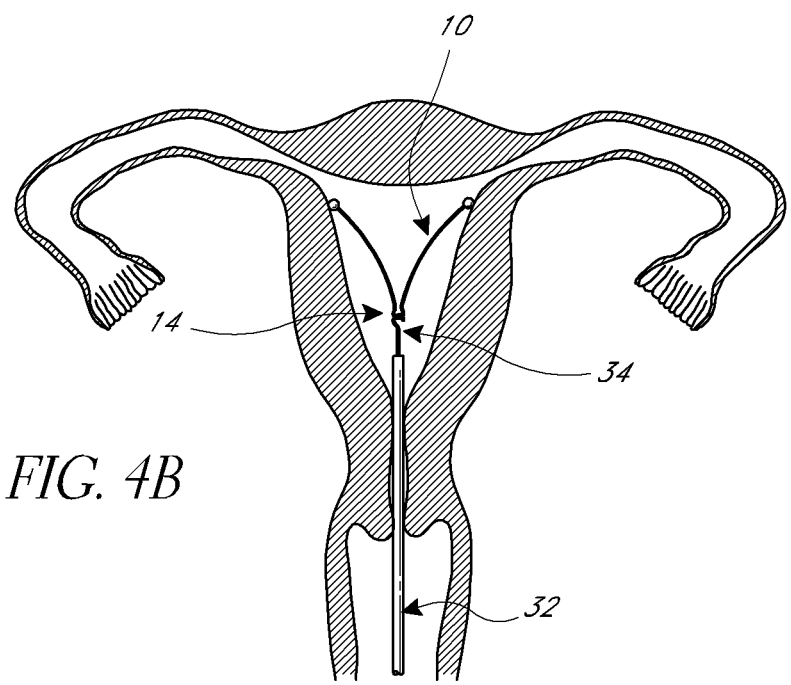
Figure 4C:
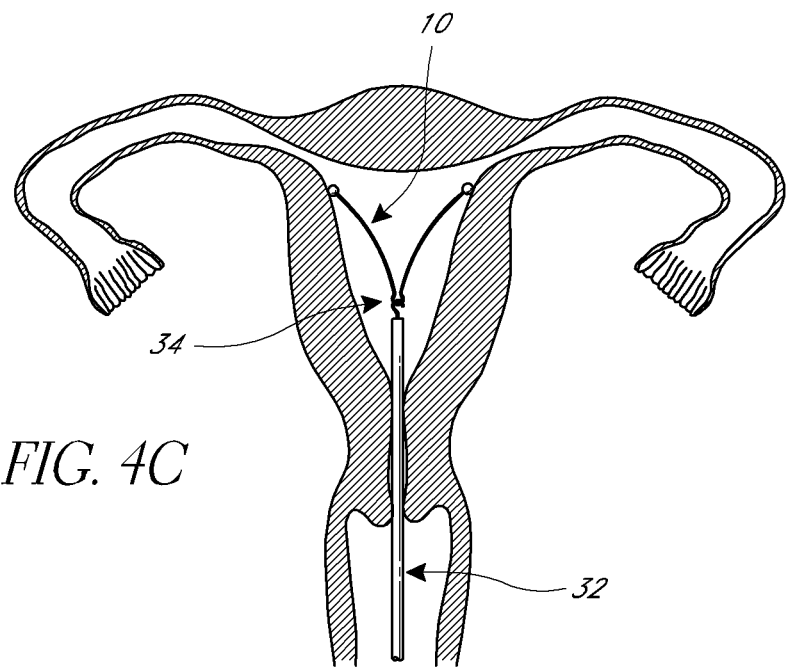
Figure 4D:
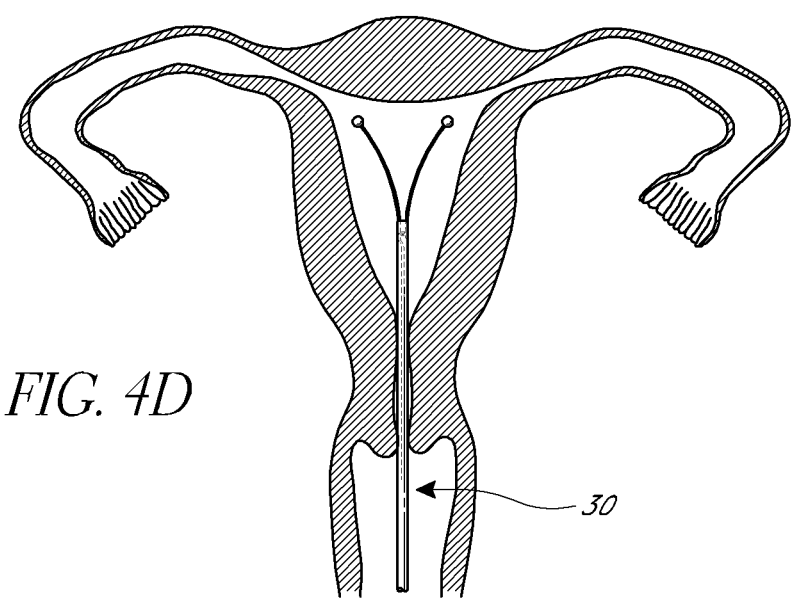
Figure 4E:
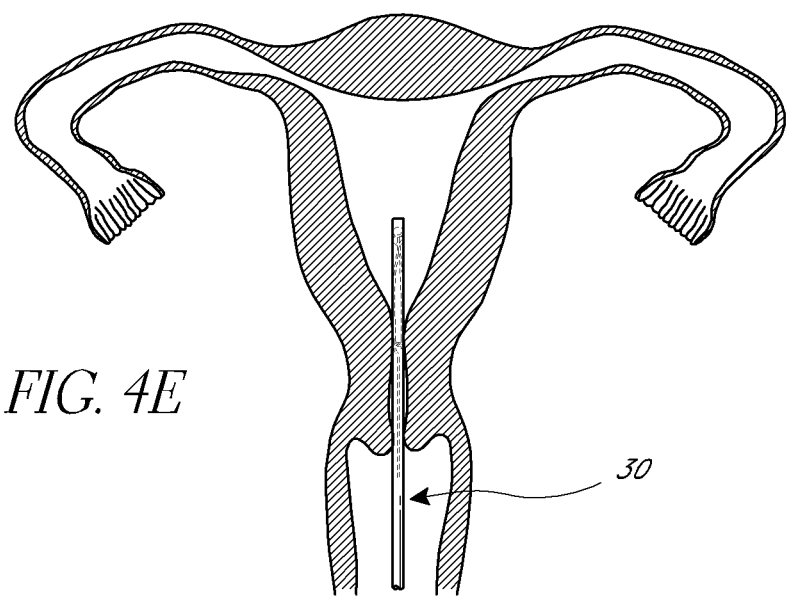
Figure 4F:
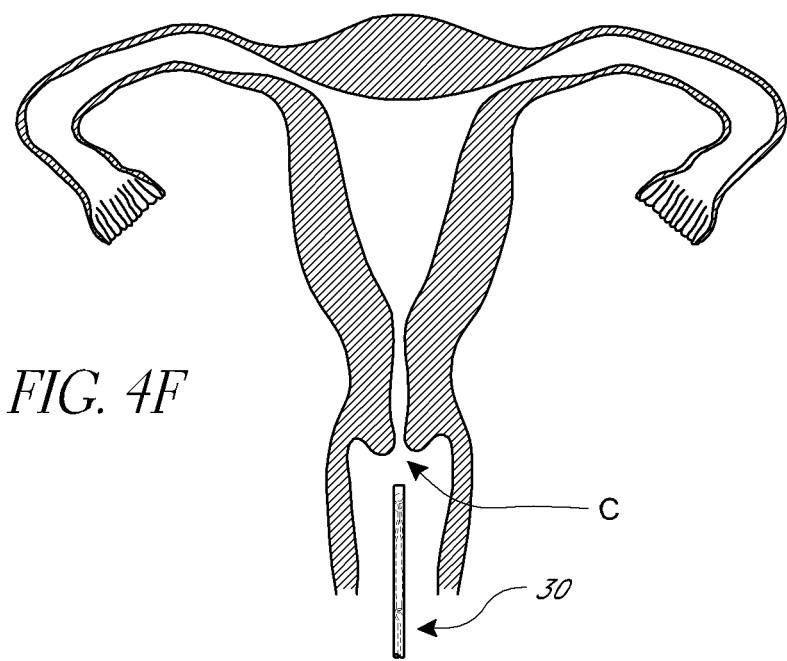

FIG. 4B shows hook 34 coupled with spring portion 14 of IUD 10. FIGS. 4C and 4D show hook 34 being retracted into catheter body 32 to pull IUD 10 into catheter body 32. FIG. 4E shows IUD 10 retracted fully into catheter body 32. Finally, FIG. 4F shows IUD 10 and removal device 30 removed from the uterus U through the cervix C. Using this method, IUD 10 may be easily removed from the uterus U in a physician's office with or without visualization techniques such as ultrasound.

Figure 5:
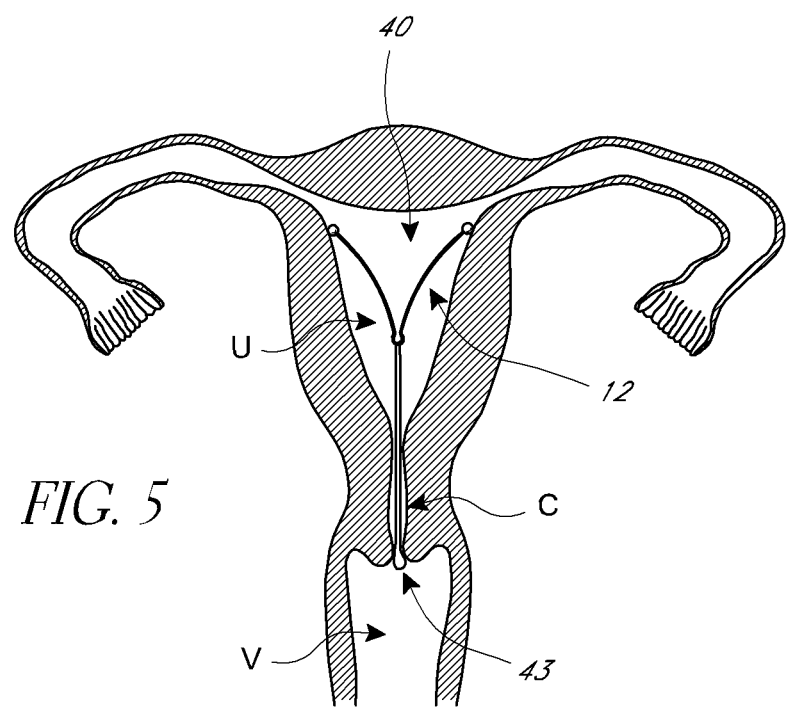
FIG. 5 shows a cross-sectional view of a uterus, cervix and fallopian tubes, illustrating an alternative embodiment of an IUD.

FIG. 5 shows an alternative embodiment of an IUD 40, including an attached thread 43. Thread 43 may be attached to elongate body 12 and may be made of surgical-grade suture material, for example, such as a monofilament polyethylene material. Thread 43 is typically long enough to extend from IUD 40 through the cervix C and into the vagina V. Thus, IUD 10 may be removed by simply grasping surgical thread 43 with standard forceps, fingers, or other tool and pulling IUD 40 out of the uterus U through the cervix C.

Figure 6:
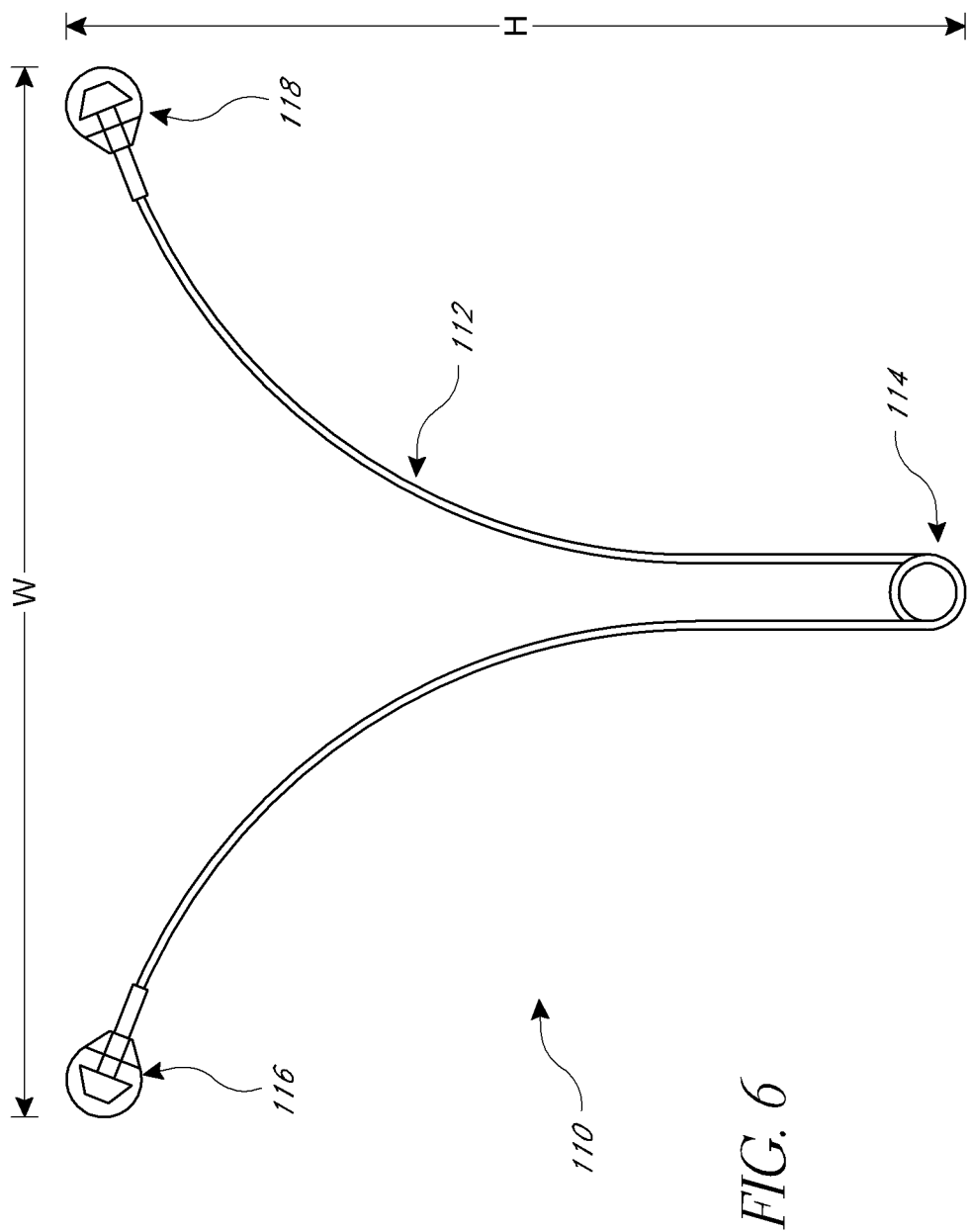
FIG. 6 is a front view of an intrauterine device (IUD), according to an alternative embodiment.

Referring now to FIG. 6, an alternative embodiment of an IUD 110 may include a resilient elongate member 112, spring portion 114 located approximately at a midpoint along elongate member 112, and two tissue contact members 116, 118 located at opposite ends of elongate member 112. In this embodiment, IUD 110 is taller (or "longer") than the previously described IUD 10. As previously discussed in reference to other embodiments, IUD 110 may have a height H and a wingspan W. The height H of IUD 110, according to one embodiment, may be between about 25 mm and about 35 mm, and the wingspan W may be between about 40 mm and about 50 mm. This is in contrast to IUD 10, which has a height H between about 25 mm and about 28 mm and a wingspan W of between about 44 mm and about 46 mm. IUD 110 may work better in some women for migration prevention and/or contraceptive effect, based on anatomical variations of the uterus between women.

In some embodiments, multiple different sizes and/or shapes of IUDs 10, 110 may be provided together as a system or kit. Alternatively, different sizes and/or shapes may be provided separately. A variety of sizes/shapes may allow a physician to choose a size and shape for a particular patient, based on that patient's anatomy.

Figure 7A:
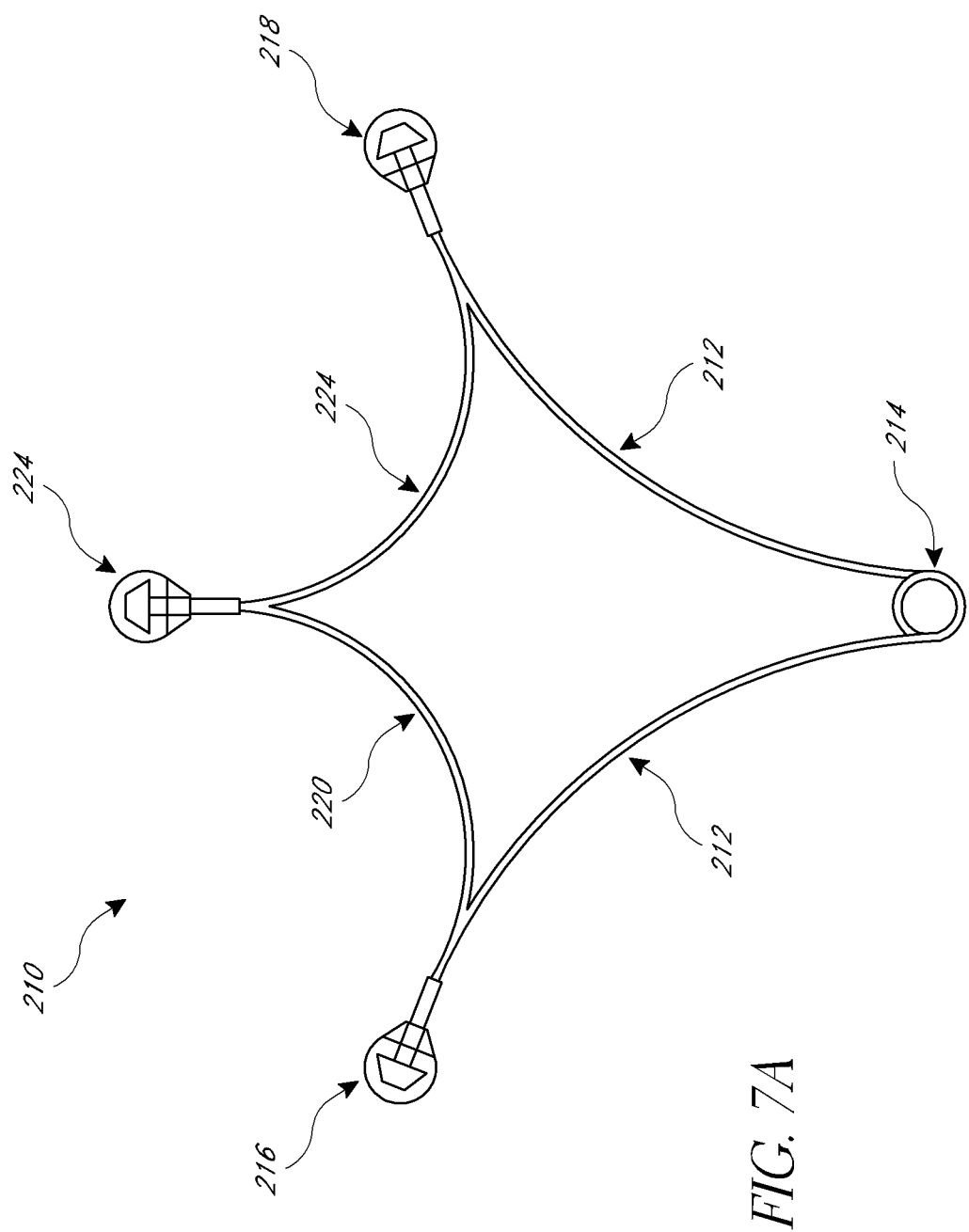
FIG. 7A is a front view of an intrauterine device (IUD) having an additional tissue contact member for contacting a fundus of a uterus, according to another alternative embodiment.

With reference now to FIG. 7A, in another embodiment, an IUD 210 may include one or more fundus contact members 224, in addition to two or more tissue contact members 216, 218. The fundus is the upper part of the uterus, and fundus contact member(s) 224 are generally configured to contact tissue of the inner uterine wall at the fundus of the uterus. In the embodiment shown, IUD includes a first resilient member 212 with a spring portion 214, tissue contact members 216, 218 located at opposite ends of first resilient member 212, one fundus contact member 224, a second resilient member 220 disposed between one tissue contact member 216 and fundus contact member 224, and a third resilient contact member 222 disposed between the other tissue contact member 218 and fundus contact member 224. First resilient member 212, spring portion 214, and tissue contact members 216, 218 may be very similar to or the same as the analogous features of IUD 10 described previously. Fundus contact member 224 is an optional feature configured and positioned to contact the fundus of the uterus when IUD 210 resides in the uterus. Contacting the fundus may provide enhanced contraceptive effects and may also help maintain IUD 210 in a desired position in the uterus, relative to the orifices of the fallopian tubes. Second resilient member 220 and third resilient member 222 may be made of Nitinol and may act primarily to support fundus contact member 224 and to lend additional structural integrity to IUD 210.

Figure 7B:
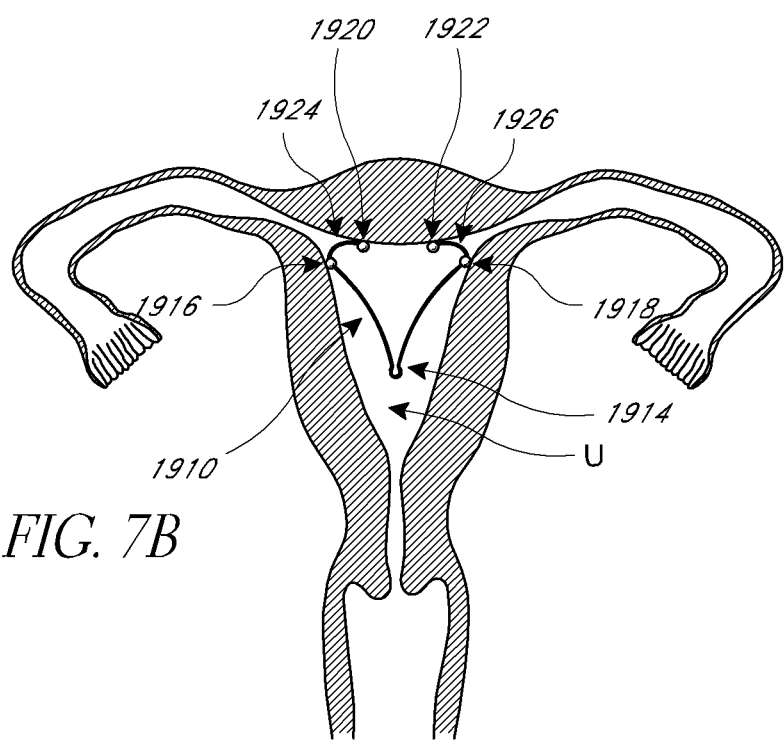
FIG. 7B is a front view of an intrauterine device (IUD) having two additional tissue contact members for contacting a fundus of a uterus, according to another alternative embodiment.

Referring now to FIG. 7B, an alternate embodiment of an IUD 1910 may include two fundus contact members 1920, 1922. This embodiment includes an elongate member 1912, a spring portion 1914, two tissue contact members 1916, 1918, and two fundus contact members 1920, 1922, which may be attached to tissue contact members 1916, 1918 via secondary elongate members 1924, 1926, which may also be made of Nitinol. As just mentioned, fundus contact members 1920, 1922 may enhance the contraceptive effects of IUD and/or help maintain IUD 1910 in a desired position in the uterus. Fundus contact members 1920, 1922 may be made of similar or the same material as tissue contact members and may have the same or similar shape and size as tissue contact members, at least according to one embodiment.

Figure 7C:
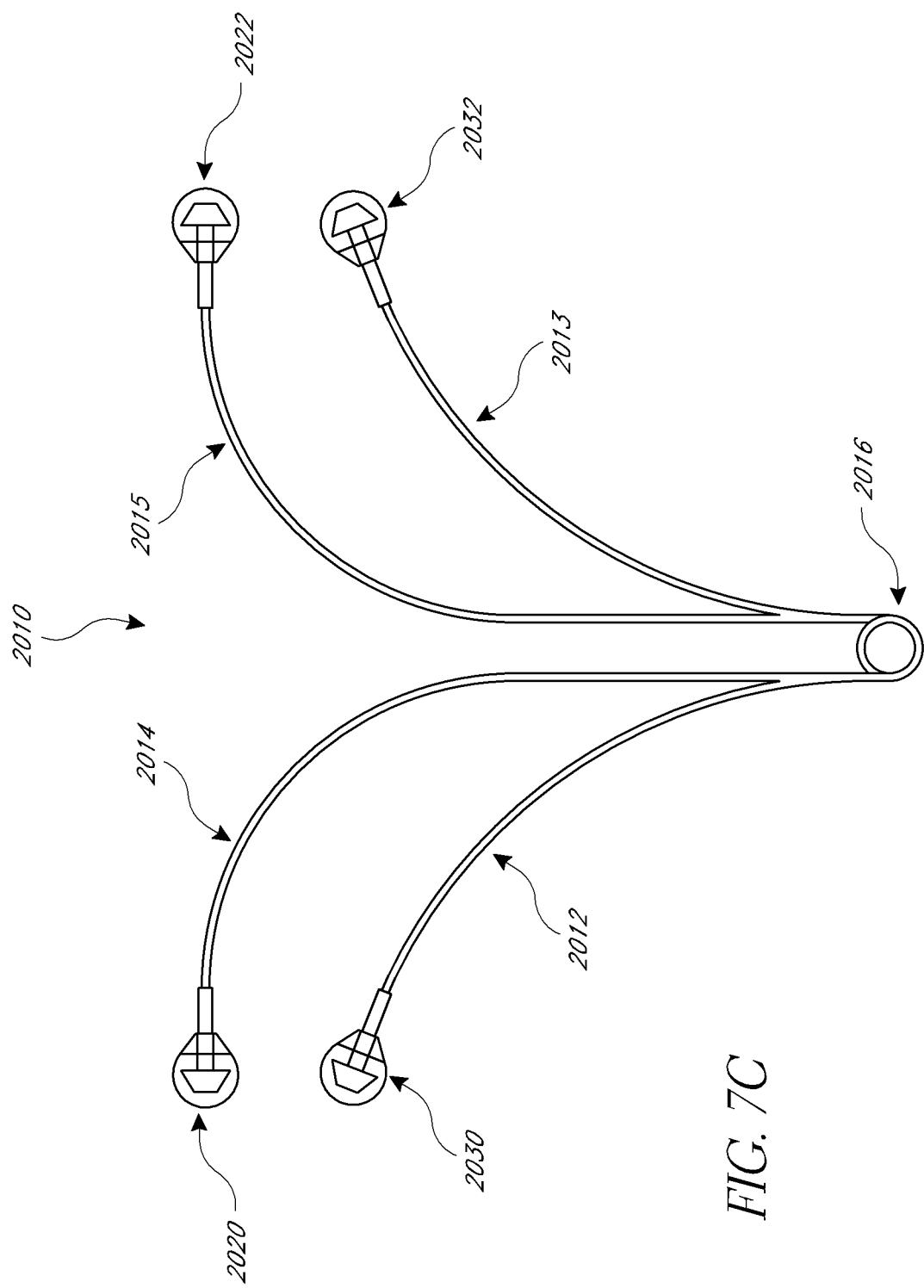
FIG. 7C is a front view of an intrauterine device (IUD) having two additional tissue contact members for contacting a fundus of a uterus, according to another alternative embodiment.

With reference now to FIG. 7C, in yet another alternative embodiment, IUD 2010 may again include two fundus contact members 2020, 2022. In this embodiment, however, IUD 2010 includes four resilient arms 2012, 2013, 2014, 2015 extending from a spring portion 2016. Two arms 2012, 2013 have tissue contact members 2030, 2032 at their ends, and two arms 2014, 2015 have fundus contact members 2020, 2022 at their ends. Of course, both tissue contact members 2030, 2032 and fundus contact members 2020, 2022 contact tissue of the inner wall of the uterus during use. Fundus contact members 2020, 2022 are simply configured to contact the particular fundus portion of the uterine wall tissue. In this embodiment, the distance from the bottom of spring portion 2016 to the top of tissue contact members 2030, 2032 may be said to delineate a first height H1, and the distance from the bottom of spring portion 2016 to the top of fundus contact members 2020, 2022 may be said to delineate a second height H2. In one embodiment, for example, height H1 may be between about 25 mm and about 28 mm, and height H2 may be between about 27 mm and about 35 mm. According to one embodiment, the wingspan (or "width") W of IUD 2010 may be between about 40 mm and about 50 mm. The combination of tissue contact members 2030, 2032 and fundus contact members 2020, 2022 may help promote contraception, enhance stability and/or help maintain position of IUD 2010.

Figure 8:
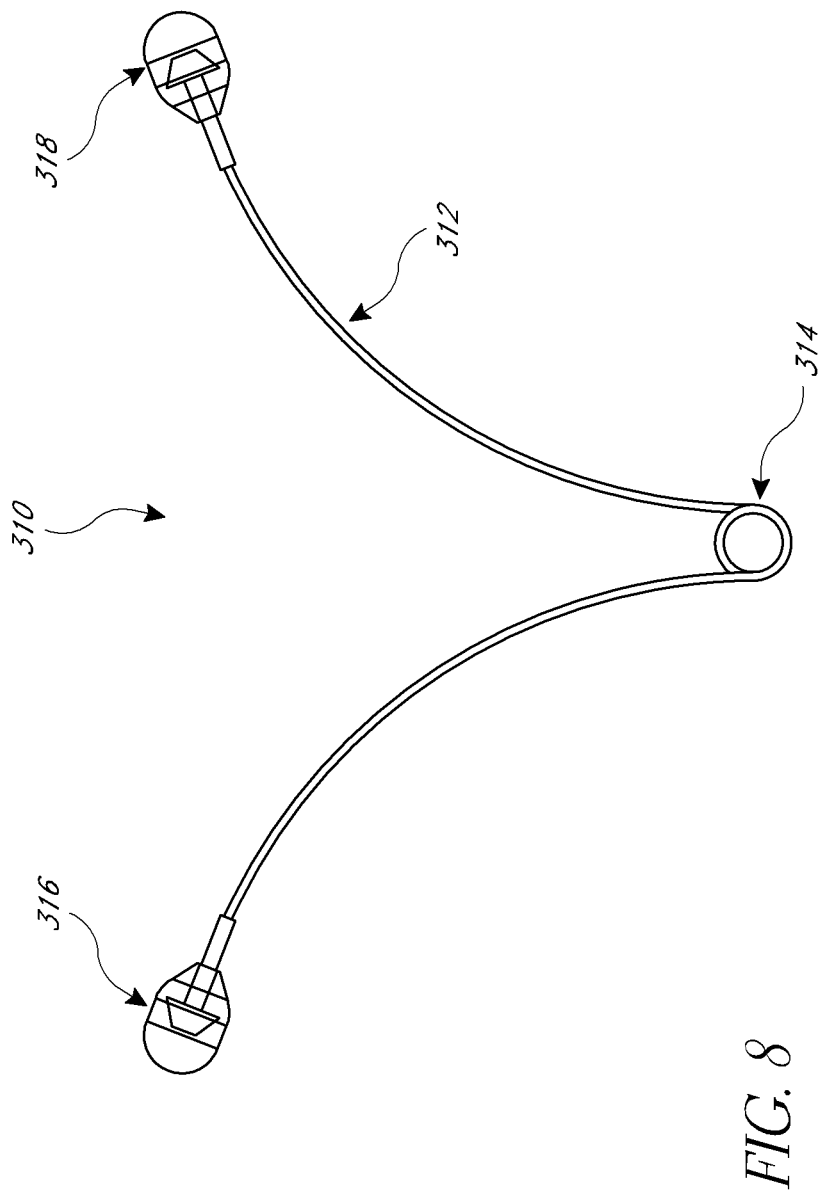
FIG. 8 is a front view of an intrauterine device (IUD), according to another alternative embodiment.

Referring now to FIG. 8, another embodiment of an IUD 310 includes a resilient elongate member 312 with a spring portion 314, both similar to or the same as those described in reference to IUD 10. In this embodiment, however, tissue contact members 316, 318 have a larger surface area than those previously described. For example, the surface area of each tissue contact member 316, 318 in this embodiment may be between about 42 mm squared and about 43 mm squared. As mentioned previously, the surface area of tissue contact members 316, 318 may be selected to prevent tissue in-growth, prevent uterine wall perforation, minimize or eliminate pain, and/or help prevent migration (i.e., maintain the position of IUD 310 within the uterine cavity in a desired location). Tissue contact members 316, 318 with a larger surface area may help achieve at least some of these goals.

Figure 9:
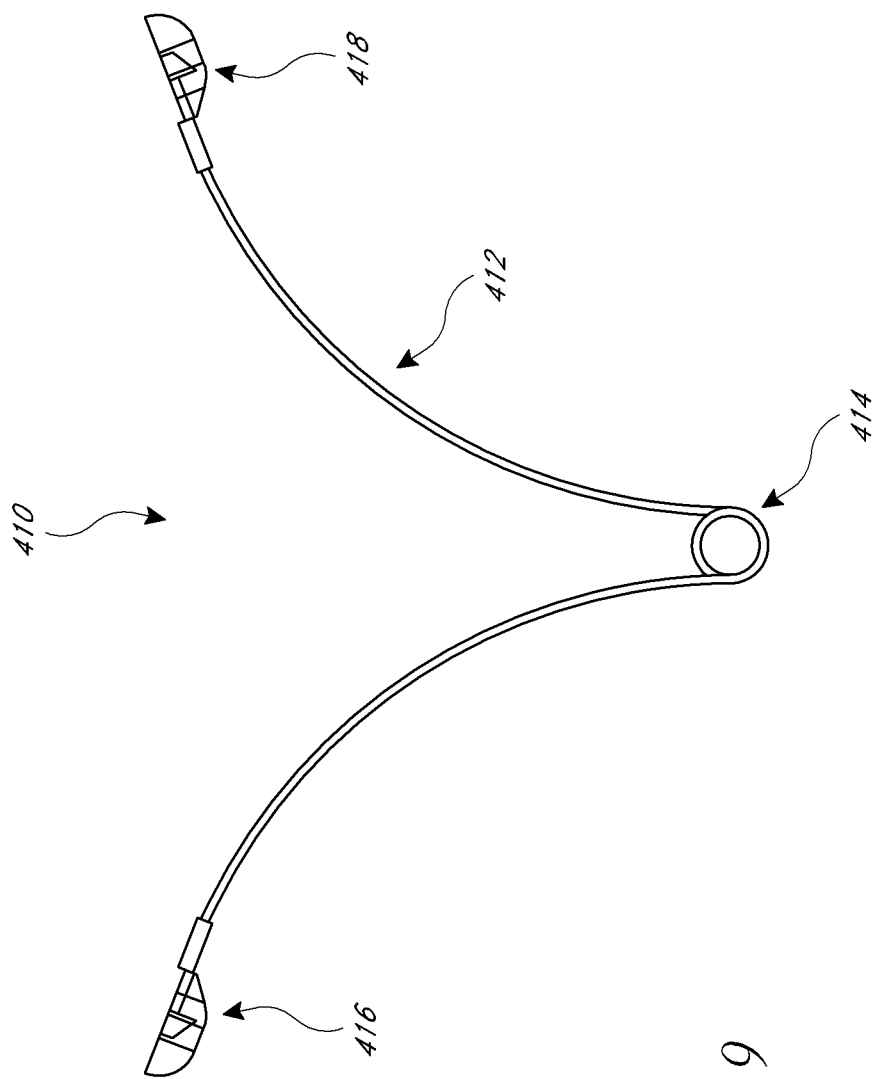
FIG. 9 is a front view of an intrauterine device (IUD), according to another alternative embodiment.

FIG. 9 illustrates another alternative embodiment of an IUD 410. In this embodiment, resilient elongate member 412 and spring portion 414 are as previously described, but tissue contact members 416, 418 have been approximately cut in half, length-wise, relative to tissue contact members 316, 318 shown and described in FIG. 8. This embodiment may be used to increase the ratio of surface area to volume of tissue contact members 416, 418, which may help achieve at least some of the above-stated goals.

Figure 10B:
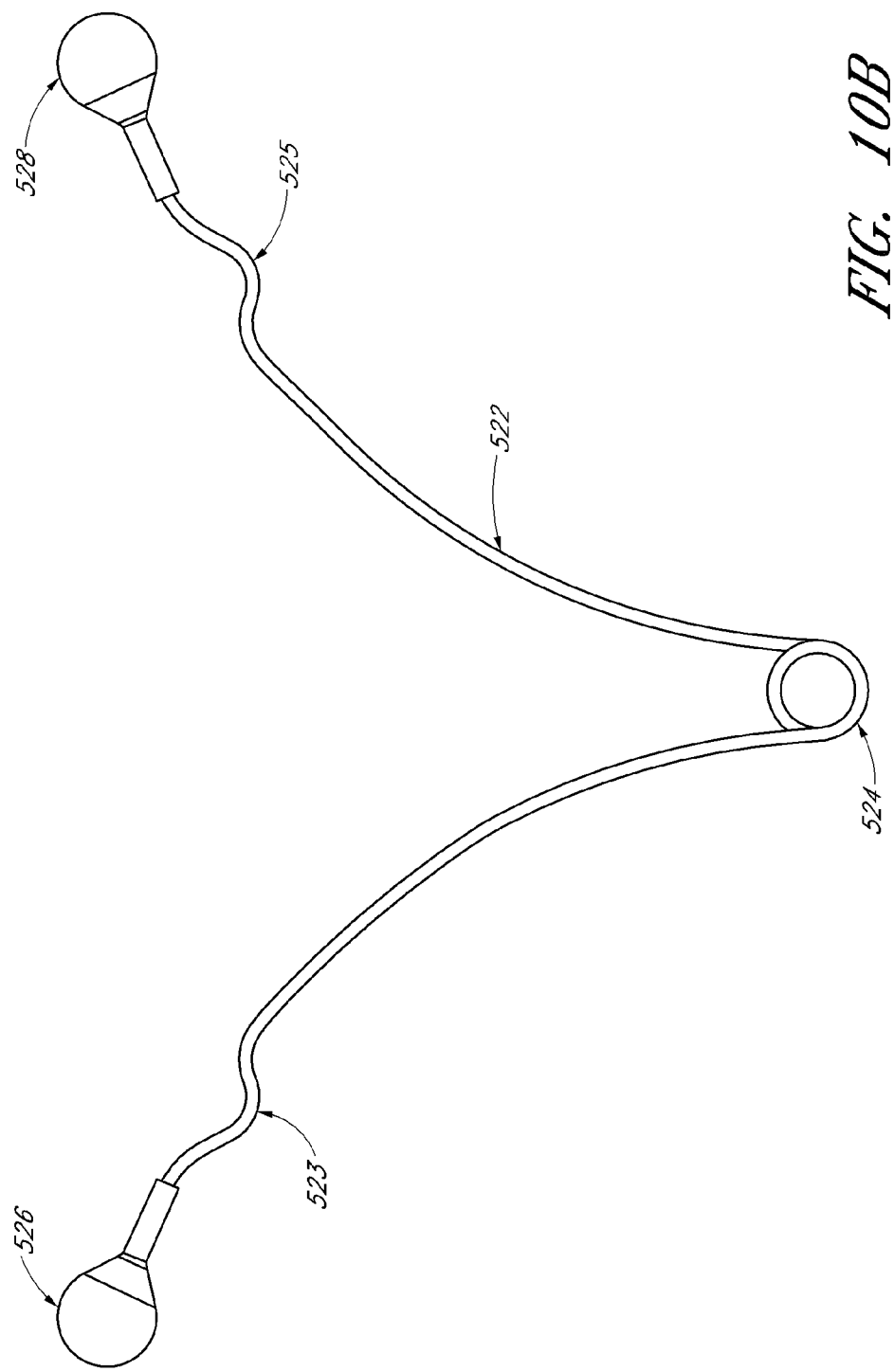
FIG. 10B is a front view of an intrauterine device (IUD) having bends in an elongate member thereof, according to another alternative embodiment.
Figure 10C:
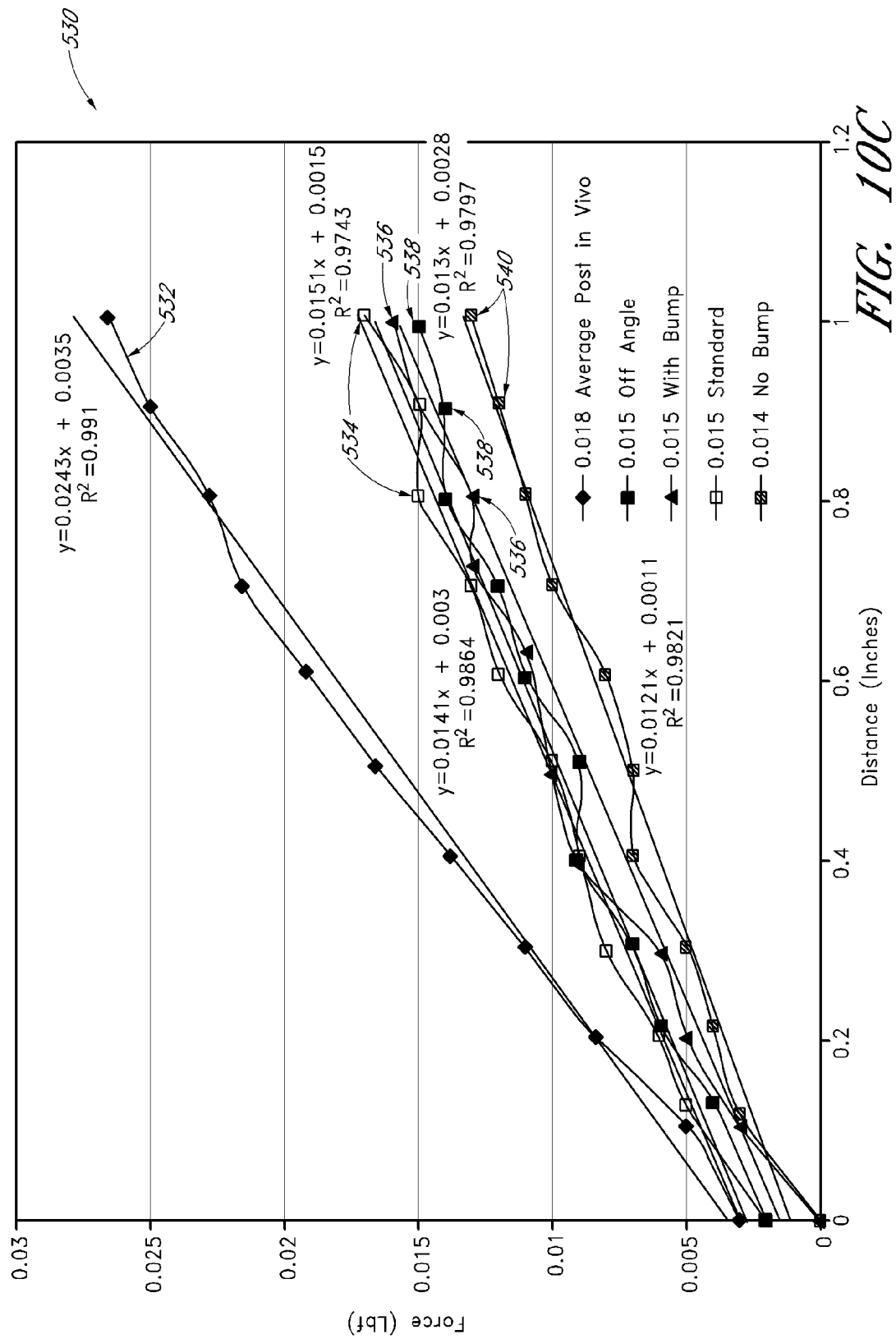
FIG. 10C is a chart showing force versus displacement in various embodiments of an intrauterine device.
Figure 11A:
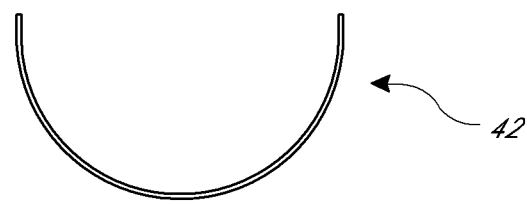
FIGS. 11A-11D are front views of elongate members of IUDs, according to four alternative embodiments.
Figure 11B:
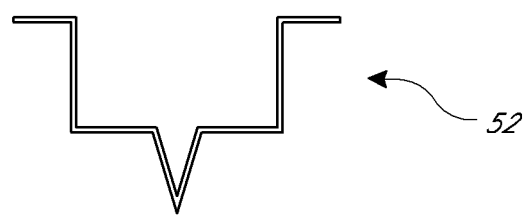
Figure 11C:
Figure 11D:
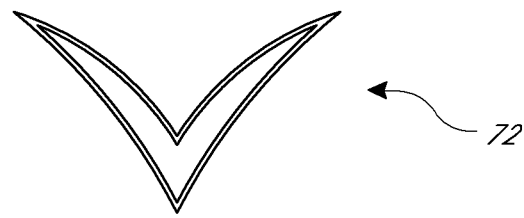

Referring to FIGS. 10A-10C, various alterations may be made to an embodiment of an IUD to provide a desired amount of total lateral force generated by compression of the two tissue contact members toward each other when the device is in the default expanded configuration. This force may be measured, for example, using a spring force measurement device manufactured by Instron® or any other suitable force measurement device. For all the reasons described previously herein, the IUD may be configured to apply an amount of force specifically to promote contraception, avoid migration of the device, and also avoid perforation of the uterine wall. To do so, the IUD may have a shape, size, and diameter of Nitinol forming its elongate member, which are all designed to provide a desired amount of lateral force generation.

Referring now to FIG. 10A, one embodiment of an IUD 510 may include a resilient elongate member 512 having a spring portion 514 and intermediate bends 513, 515, and two tissue contact members 516, 518 disposed at opposite ends of elongate member 512. Bends 513, 515 (also referred to as "off angle bends") may act to slightly reduce the laterally directed force, thus further reducing the risk of perforation while still maintaining sufficient opening force to allow IUD 510 to fully expand upon exiting the delivery device. Although the embodiment shown includes two bends 513, 515, in alternative embodiments elongate member 512 may include any suitable number of bends. This embodiment of IUD 510 may also be taller than IUD 10, having a height H of between about 30 mm and about 32 mm.

Referring now to FIG. 10B, an alternative embodiment of an IUD 520 may include a resilient elongate member 522 having a spring portion 524 and intermediate bends 523, 525, and two tissue contact members 526, 528 disposed at opposite ends of elongate member 522. Bends 523, 525 (also referred to as "bumps") may act to slightly reduce the laterally directed force, thus further reducing the risk of perforation while still maintaining sufficient opening force to allow IUD 520 to fully expand upon exiting the delivery device. Although the embodiment shown includes two bends 523, 525, in alternative embodiments elongate member 512 may include any suitable number of bends.

With reference now to FIG. 10C, a chart 530 includes a number of force vs. displacement curves measured for a number of different embodiments of an IUD. Each of the tested embodiments had the same height and width, but varied in wire diameter and elongate member configuration. Force in pounds is displayed on the y-axis, and distance in inches is displayed on the x-axis. To make these measurements, the device is placed in its default expanded configuration, one of the tissue contact members is placed against a solid surface, and the other is placed against the surface of a load cell. Force measured by the load cell is recorded as a function of compression distance as the surface of the load cell and the solid surface are moved toward each other. The distance measurement along the x-axis of FIG. 10C is a measure of how much closer together the tissue contact members are from the fully expanded configuration which corresponds to a distance of zero in FIG. 10C. A distance value in FIG. 10C of one inch therefore refers, for example, to a decrease in distance between the two tissue contact members of one inch from the fully expanded configuration. The top-most, "0.018 Average Post In Vivo" line 532 was measured for an IUD having a Nitinol elongate body with a 0.018-inch diameter and no bends in the elongate members such as is shown in FIG. 1. As shown in the chart, this embodiment has the highest force generation of the tested embodiments (although of course higher forces could be generated with different embodiments). In testing, the inventors found that this 0.018-inch diameter embodiment tended to apply an amount of laterally directed force in the uterus that caused the tissue contact members to travel distally toward and sometimes into the fallopian tubes, which is not generally desired for the IUDs described herein. Therefore, further embodiments having lesser amounts of force generation were developed and tested.

The "0.015 Off Angle" line 534 in chart 530 represents an IUD having a Nitinol elongate body with a 0.015-inch diameter and two "off angle" bends, such as IUD 510 pictured in FIG. 10A. The "0.015 with Bump" line 536 in chart 530 represents an IUD having a Nitinol elongate body with a 0.015-inch diameter and two "bump" bends, such as IUD 520 pictured in FIG. 10B. The "0.015 Standard" line 538 represents an IUD such as IUD 10 from FIG. 1, having a Nitinol elongate body with a 0.015-inch diameter and no bends. Finally, the "0.014" line 540 represents an IUD having a configuration such as IUD 10 with a Nitinol elongate body having a 0.014" diameter. Thus, chart 530 demonstrates that altering the shape or diameter (or both) of an IUD will typically affect its ability to generate laterally directed force. It may be advantageous to provide an amount of force represented by the lower four lines 534, 536, 538, 540 rather than the upper line 532, according to some embodiments. Thus, it has been found that a wire diameter of less than 0.018 mm, and advantageously between about 0.014 and 0.015 mm appears to be especially suitable for these IUD devices.

Referring now to FIGS. 11A-11D, the resilient elongate member incorporated in an IUD, according to various alternative embodiments, may have any of a number of suitable configurations. For example, an elongate member 42 may have a U-shape as in FIG. 11A, an elongate member 52 may have a stepped configuration as in FIG. 11B, an elongate member 62 may have a crescent shape as in FIG. 11C, or an elongate member 72 may have a chevron shape as in FIG. 11D.

Figure 12A:
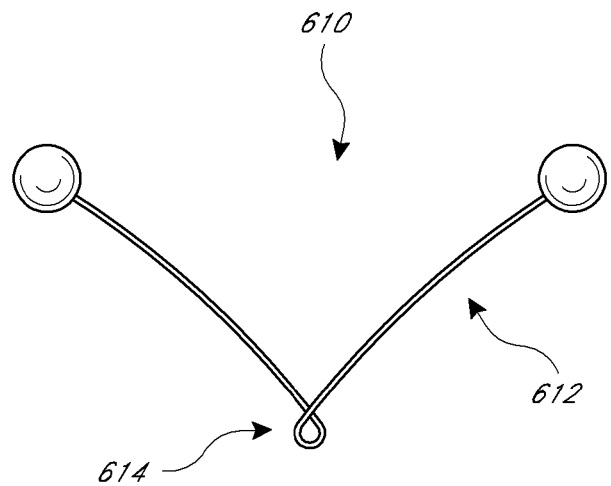
FIGS. 12A and 12B are front views of two alternative embodiments of an IUD, each having a different spring portion.

With reference now to FIG. 12A, in various embodiments, an IUD 610 may have an elongate member 612 with a spring portion 614 having any of a number of different shapes. Spring portion 614 in this embodiment is simply a single coil.

Figure 12B:
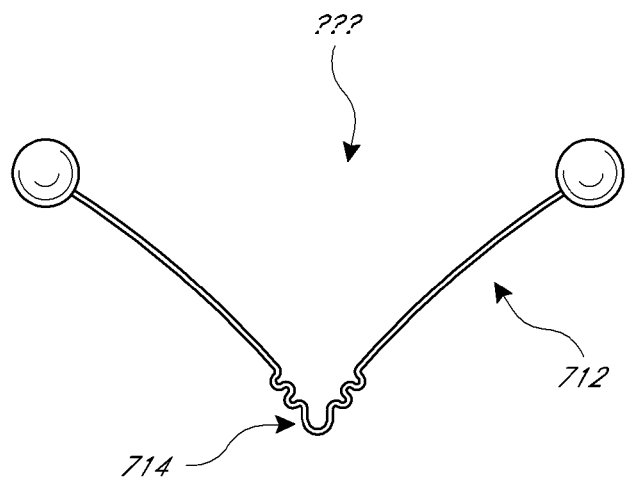

FIG. 12B illustrates another alternative embodiment of IUD 710. In this embodiment, an elongate member 712 includes a spring portion 714 with multiple, small bends 714.

Figure 13:
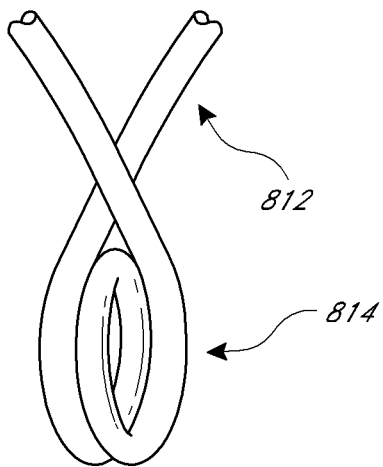
FIG. 13 is a perspective view of a spring portion of an IUD, according to one embodiment.
Figure 14A:
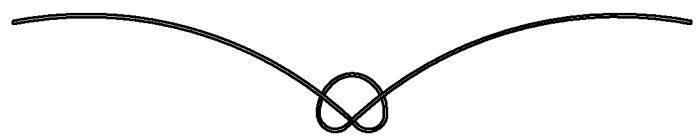
FIGS. 14A-K are front views of elongate members of IUDs, according to various alternative embodiments having differently configured spring force generating portions.
Figure 14B:
Figure 14C:
Figure 14D:
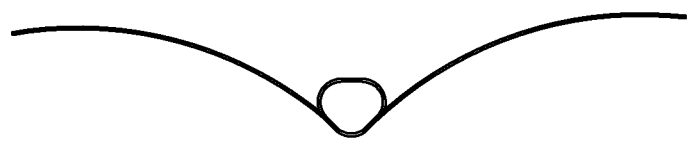
Figure 14E:
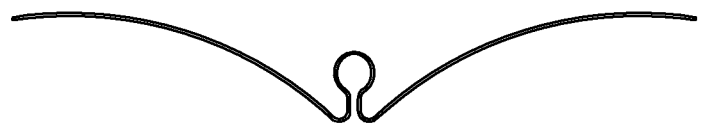
Figure 14F:
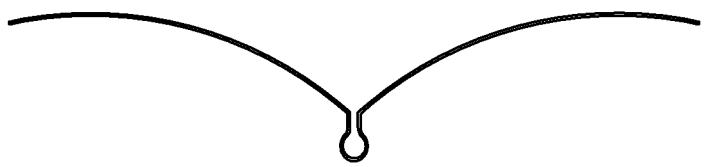
Figure 14G:
Figure 14H:
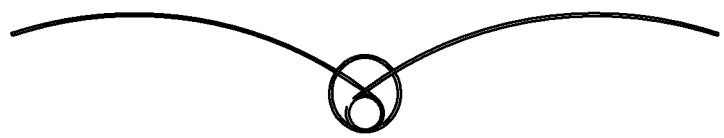
Figure 14I:
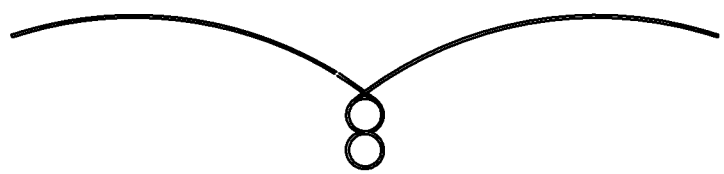
Figure 14J:
Figure 14K:
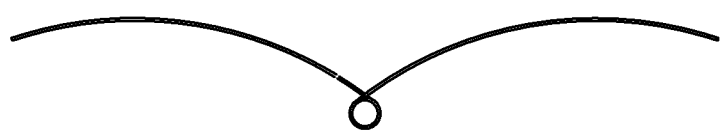
Figure 15A:
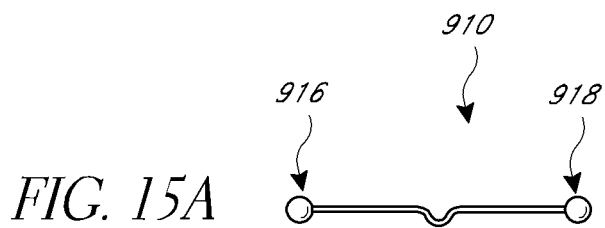
FIGS. 15A-15D show an alternative embodiment of an IUD alone, housed in a delivery device, partially released from the delivery device, and implanted in a uterus, respectively, according to one embodiment.

FIG. 13 illustrates in close-up another alternative embodiment of a spring portion 814 of an elongate member 812. In this embodiment, spring portion 814 is configured as a two-coil spring.

Referring now to FIGS. 14A-14K, a number of embodiments of elongate members, each having differently configured spring portions, are shown. Any suitable configuration of a spring portion may be used to confer the desired amount of spring force to an IUD.

Figure 15B:
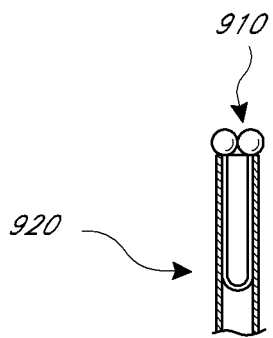
Figure 15D:
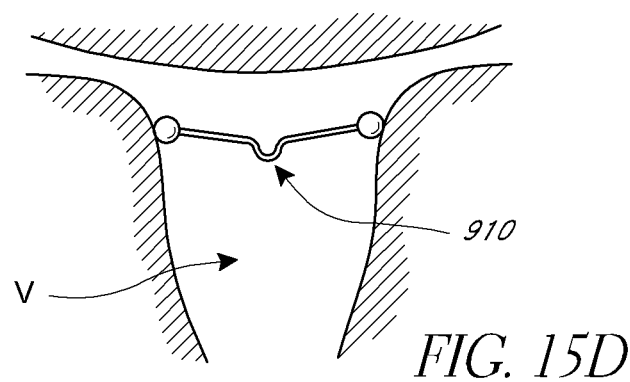
Figure 15C:
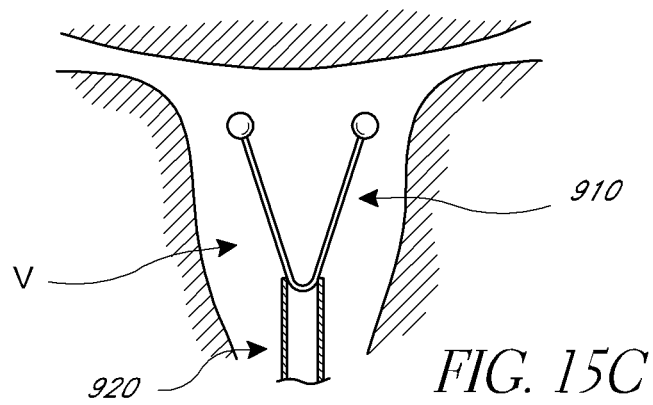

With reference now to FIGS. 15A-15D, in another embodiment, an IUD 910 may include a resilient elongate member 912 with a spring portion 914 and two tissue contact members 916, 918 disposed at opposite ends of elongate member 912. In this embodiment, elongate member 912 is predominantly straight, aside from spring portion 914 that forms a bend. FIG. 15B shows IUD 910 disposed in a delivery device 920. FIG. 15C shows IUD 910 being delivered out of delivery device 920 into a uterus. FIG. 15D shows IUD 910 fully delivered into the uterus. This example demonstrates that an IUD 910 does not necessarily have to have a V-shape or any other particular shape as long as it has an effective amount and direction of laterally directed force.

Figure 16:
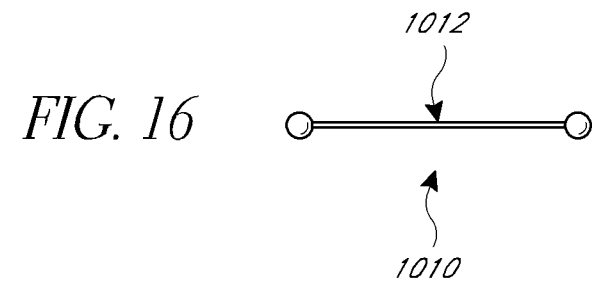
FIG. 16 is a front view of an IUD, according to an alternative embodiment.

FIG. 16 illustrates another embodiment of an IUD 1010 that is approximately a straight line without a bend or spring portion.

Figure 17A:
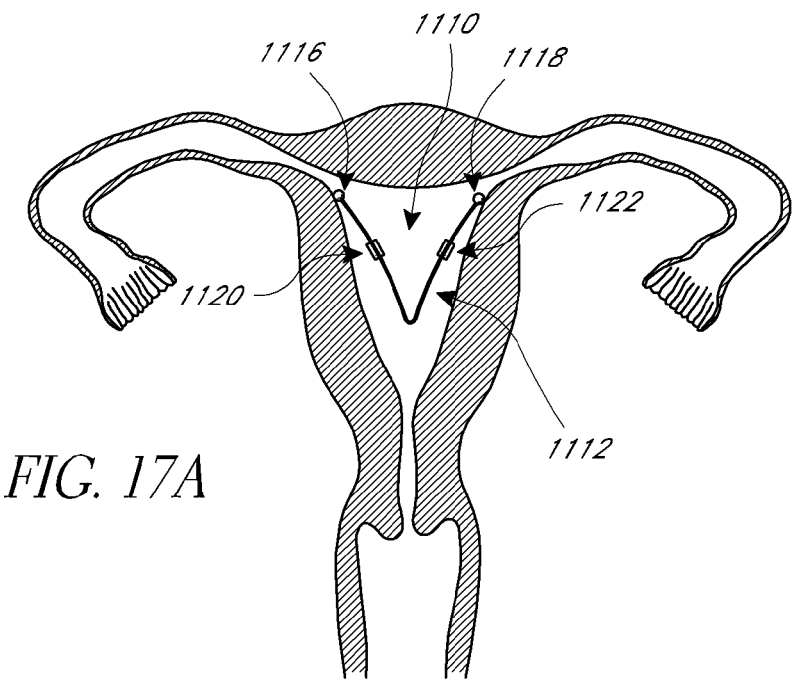
FIGS. 17A and 17B are front views of part of a female reproductive anatomy in cross section, showing an IUD having tissue contact sleeves, according to another alternative embodiment.
Figure 17B:
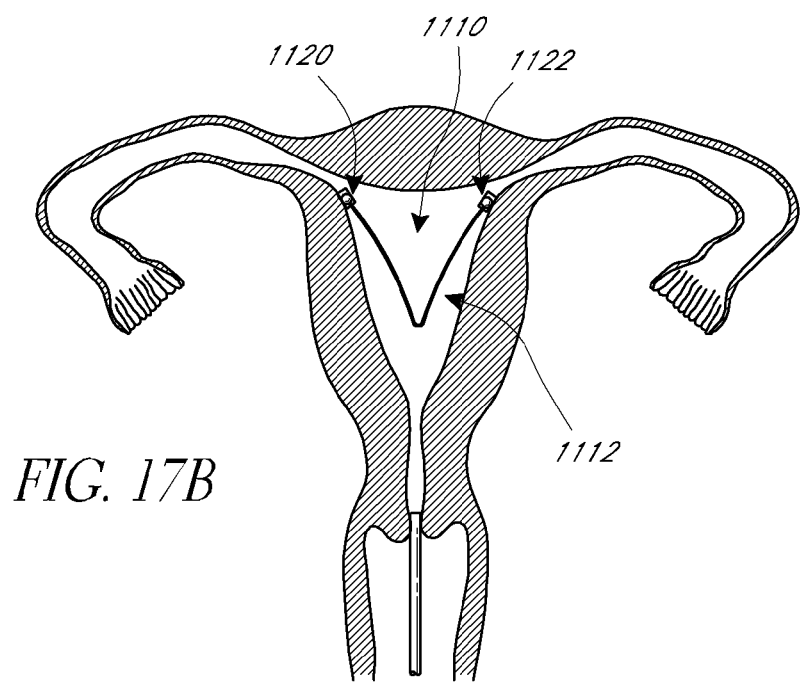

With reference now to FIGS. 17A and 17B, an alternative embodiment of an IUD 1110 is shown in place within a uterus U. In this embodiment, IUD 1110 includes an elongate member 1112, tissue contact members 1116, 1118 and tissue contact sleeves 1120, 1122. Tissue contact sleeves 1120, 1122 advance along elongate member 1112 and over tissue contact members 1116, 1118 to contact the uterine wall W. Sleeves 1120, 1122 may serve, for example, to increase the surface area over which uterine wall W is contacted by IUD 1110. This may help prevent tissue in-growth of tissue contact members 1116, 1118, thus facilitating removal of IUD 10 at a later date. Sleeves 1120, 1122 may be advanced into position using an advancement tool (not shown) delivered through delivery device 20, for example.

Figure 18A:
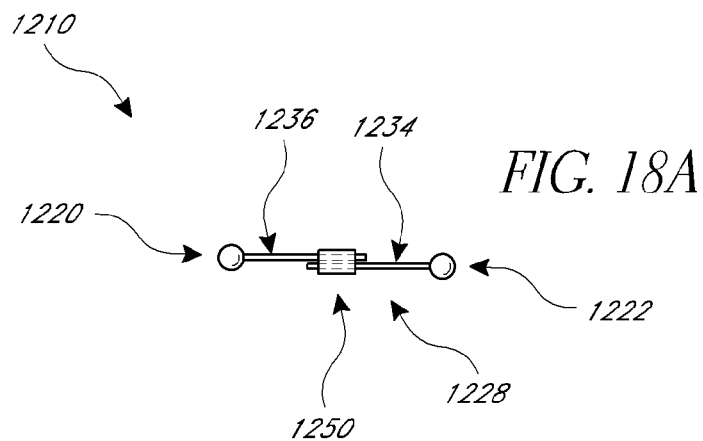
FIGS. 18A-18C show an alternative embodiment of an IUD alone, implanted in a uterus, and being adjusted, respectively, according to one embodiment.
Figure 18B:
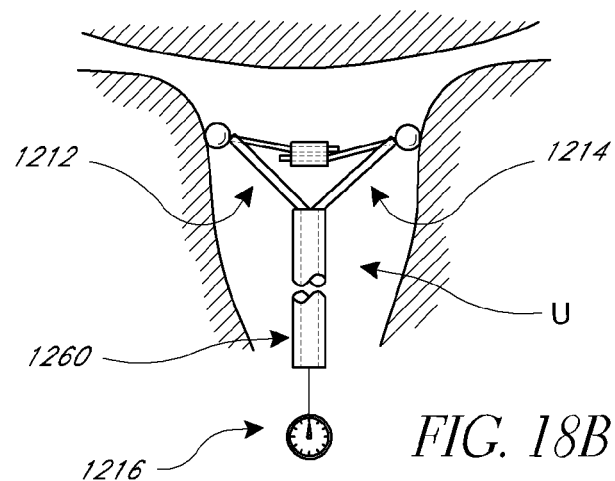
Figure 18C:
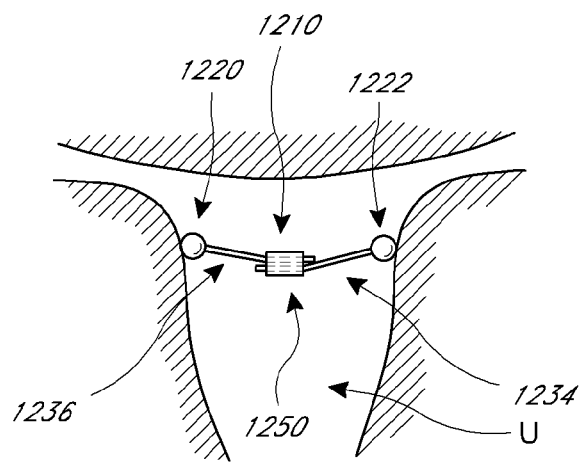

Referring now to FIGS. 18A-18C, some embodiments of an IUD 1210 may include other mechanical mechanisms for providing spring force rather than spring portions of an elongate members. With reference to FIG. 18A, IUD 1210 may include an elongated member 1228 composed of first and second legs 1234, 1236 connected to each other for controlled relative movement by a clamping member 1250. Until the clamping member 1250 is crimped to lock the first and second legs 1234, 1236 in position, clamping member 1250 permits relative movement of the first and second legs 1234, 1236, and ultimately, first and second tissue contact members 1220, 1222. IUD 1210 may be delivered using a delivery device 1260 as shown with reference to FIG. 18B. Delivery device 1260 includes first and second members 1212, 1214 which are resiliently biased outwardly to engage and force the plug members 1220, 1222 into the walls of the uterine cavity. Delivery device 1260 may be further provided with a force gauge 1216 for measuring the applied force as tissue contact members 1220, 1222 are forced outwardly into contact with the uterine wall. Alternatively, delivery device 1260 could be equipped with a force indicator such as a colored slide that moves to another position when appropriate force is achieved.

In practice, IUD 1210 may be delivered to the uterine cavity and roughly positioned in the upper part of the uterine cavity and deployed there. It then uses the shape of the uterine cavity as a guide and positions itself in the uterine cavity such that tissue contact members 1220, 1222 push slightly against the uterine wall at a position adjacent the orifices of the fallopian tubes. Delivery device 1260 may then be employed to push the first and second tissue contact members 1220, 1222 into contact with the uterine wall of the uterine cavity. When a desired application force is achieved, clamp member 1250 is crimped in a manner securing it to first and second legs 1234, 1236. Crimping of the clamping member 1250 may be achieved, for example, using medical grade forceps shaped and dimensioned to access the uterine cavity and engage clamping member 1250.

Figure 19:
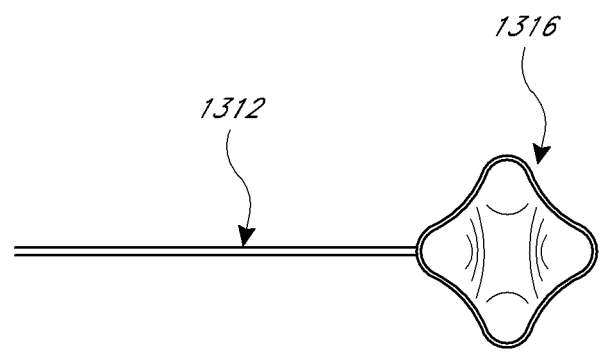
FIG. 19 is a view of part an IUD, including a tissue contact member and part of an elongate member, according to an alternative embodiment.

Referring now to FIG. 19, an alternative embodiment of a tissue contact member 1316 and a portion of an elongate member 1312 of an IUD 1310 are illustrated. In this embodiment, tissue contact member 1316 has a different shape than previously described embodiments.

Figure 20:
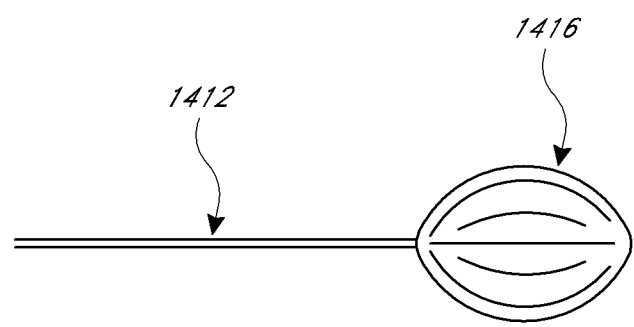
FIG. 20 is a view of part an IUD, including a tissue contact member and part of an elongate member, according to another alternative embodiment.

FIG. 20 illustrates another alternatively shaped tissue contact member 1416 disposed at a distal end of an elongate member 1412 of an IUD 1410. From these examples, it is apparent that any of a number of suitable shapes may be used for tissue contact members.

Figure 21:
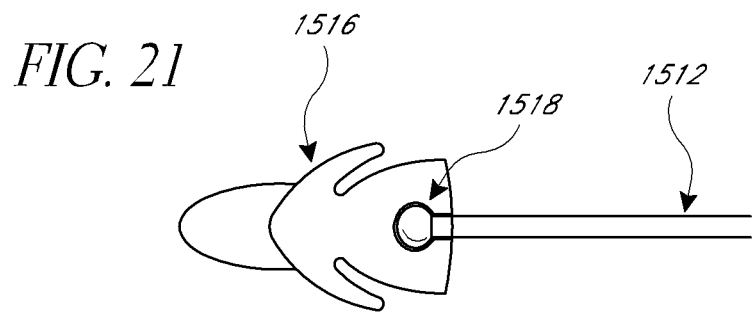
FIG. 21 is a view of part an IUD, including a tissue contact member and part of an elongate member, according to another alternative embodiment.

With reference to FIG. 21, in another embodiment, a tissue contact member 1516 may be attached to an elongate member 1512 via a ball and socket joint 1518. Ball and socket joint 1518 may provide tissue contact member 1516 with a degree of freedom to swivel and angularly align with uterine wall and thus apply more evenly distributed force.

Figure 22A:
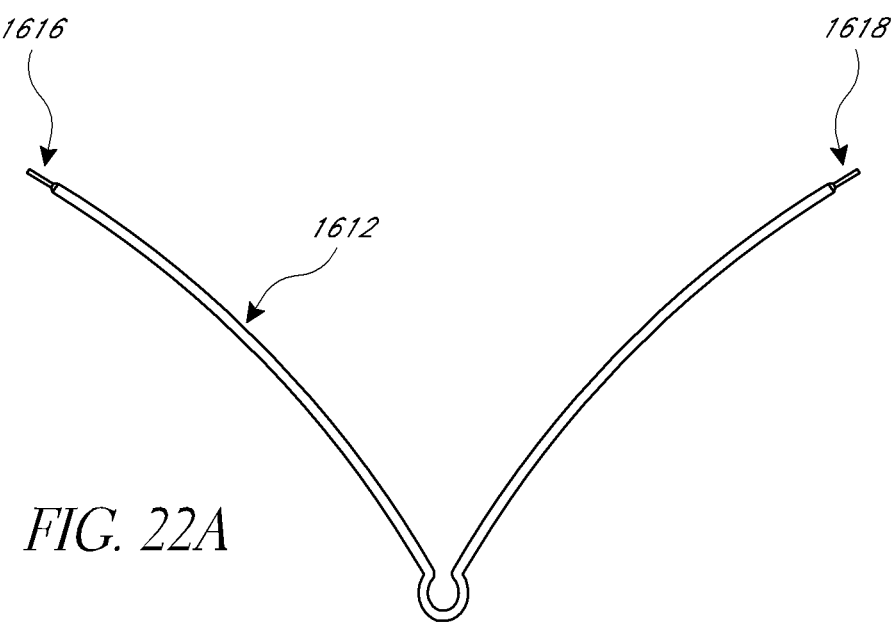
FIG. 22A is a front view of an elongate member of an IUD, according to an alternative embodiment.
Figure 22B:
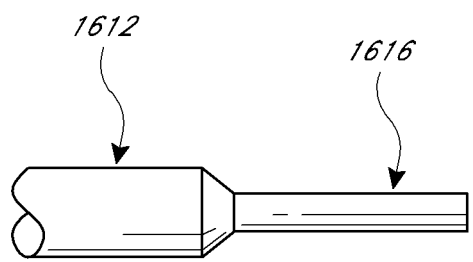
FIG. 22B is a close-up view of one end of the elongate member of FIG. 22A.

With reference to FIGS. 22A and 22B, in another alternative embodiment, an elongate member 1612 may have ends

1616, 1618 with a reduced cross section (i.e., diameter). The reduced cross section at ends 1616, 1618 may confer flexibility to tissue contact members attached thereto, thus allowing them to self-adjust to the shape of a uterine wall.

Figure 23:
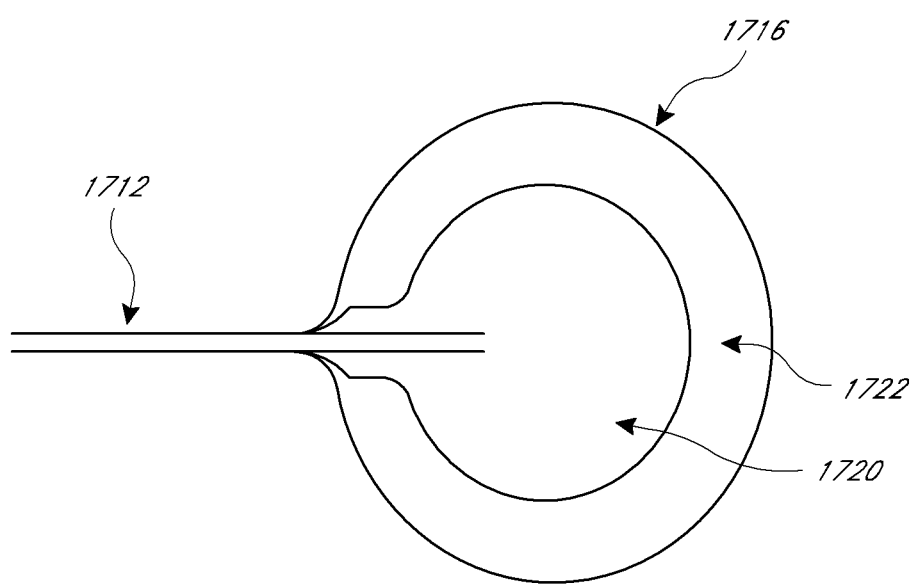
FIG. 23 is a view of part an IUD, including a tissue contact member and part of an elongate member, according to another alternative embodiment.

Referring now to FIG. 23, in another embodiment, a tissue contact member 1716 (coupled with an elongate member 1712) may be formed in a dual density configuration of various biocompatible elastomers. In one embodiment, for example, an inner portion 1720 of tissue contact member 1716 may be made from a relatively hard material, and an outer surface 1722 of tissue contact member 1716 may be made from a softer, more resilient material. Outer surface 1722, although softer than inner portion 1720, will still be designed to resist tissue in-growth while also resisting device migration.

In an alternate embodiment, outer surface 1722 may be made of a relatively hard material (for example, gelatin tablet material) temporarily affixed inner portion 1720 made of a soft pliable material (or a dual density configuration as described above) for the purpose of protecting the softer inner material. A hard outer surface 1722 may behave like a slippery surface during insertion and deployment. However, the hard material of outer surface 1722 may be composed of a bioabsorbable or decomposable (that is, expelled during normal menstrual cycle) material which quickly dissolves upon deployment within the uterus. As a result, outer surface 1722 may dissolve and be discharged or absorbed, thus allowing the soft pliable material of inner portion 1720 to ultimately seat along the uterine wall.

Figure 24:
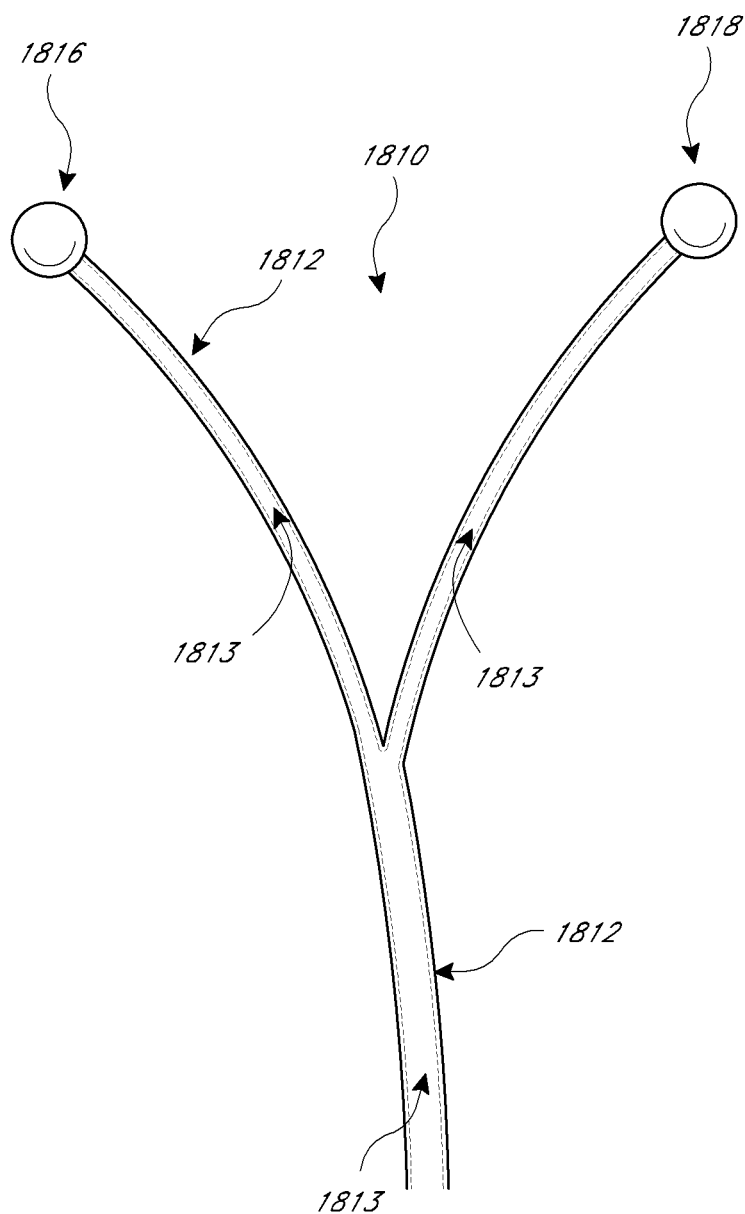
FIG. 24 is a front view of an IUD having a hollow elongate member, according to one embodiment.

Referring now to FIG. 24, in one embodiment, an IUD 1810 may include a hollow elongate body 1812 having an inner channel 1813 to provide delivery of one or more substances to the uterus. In some embodiments, such a substance (or substances) may flow through tissue contact members 1816, 1818, which may have one or more pores or a channel for fluid flow. In another embodiment, elongate body may have one or more pores or fluid outlets, so that the substance passes out of IUD 1810 into uterus via elongate body 1812. In various embodiments, any suitable substance may be provided, such as but not limited to hormones (progestin, etc.), spermicides, copper, and the like. In an alternative embodiment, tissue contact members 1816, 1818 may provide the substance via coating or via loading the substance into a porous tissue contact member 1816, 1818. In various embodiments, substance(s) may be provided to elongate body by preloading and/or by injected at the time of or immediately before or after insertion of IUD 1810 into the uterus. In one embodiment, for example, a substance may be injected into elongate member 1812 using a needle and syringe via a port on elongate member 1812 (port not shown), such as by a physician or physician's assistant.

Various embodiments of an intrauterine device and methods for using it have been disclosed above. These various embodiments may be used alone or in combination, and various changes to individual features of the embodiments may be altered, without departing from the scope of the invention. For example, the order of various method steps may in some instances be changed, and/or one or more optional features may be added to or eliminated from a described device. Therefore, the description of the embodiments provided above should not be interpreted as unduly limiting the scope of the invention as it is set forth in the claims.

What is claimed is:

1. An intrauterine device for applying force to a wall of a uterus to promote contraception without blocking the fallopian tubes, the intrauterine device comprising:

an elongate member formed of Nitinol, having a diameter between 0.010 inch and 0.025 inch, and having a default expanded configuration and a spring portion disposed approximately at a midpoint between two ends of the elongate member; wherein the elongate member comprises two elongate members that diverge away from one another; and two tissue contact members, one of which is disposed at one end of the elongate member and the other of which is disposed at the other end, wherein each tissue contact member comprises a non-porous material and has a surface area of at least 30 mm squared, wherein the intrauterine device has a width measured from a tip of one tissue contact member to a tip of the other tissue contact member of at least 40 mm in its expanded configuration outside the uterus.

2. An intrauterine device as in claim 1, wherein the default expanded configuration of the elongate member comprises a V-shape, wherein the spring portion is disposed at a vertex of the V-shape, and wherein the elongate member curves laterally from the spring portion to each of the two ends.

3. An intrauterine device as in claim 2, wherein a height of the intrauterine device measured from a bottom of the spring portion to a top of the tissue contact members is at least about 25 mm.

4. An intrauterine device as in claim 2, wherein the elongate member further
includes at least two bends configured to reduce the amount of laterally directed force, one bend disposed between the spring portion and one of the two ends, and the other bend disposed between the spring portion and the other end.

5. An intrauterine device as in claim 1, wherein the tissue contact members generate a total, laterally directed force against the wall of the uterus of between 0.002 pounds-force and 0.025 pounds-force when the intrauterine device assumes its default expanded configuration within the uterus.

6. An intrauterine device as in claim 5, wherein the tissue contact members generate a total, laterally directed force against the wall of the uterus of between 0.002 pounds-force and 0.015 pounds-force when the intrauterine device assumes its default expanded configuration within the uterus.

7. An intrauterine device as in claim 1, further comprising a substance disposed in an inner channel in the elongate member or in or on the tissue contact members.

8. An intrauterine device as in claim 7, wherein the substance is selected from the group consisting of hormones, spermicides, copper and therapeutic agents.

9. An intrauterine device as in claim 1, wherein the spring portion comprises a spring having at least one coil formed in the elongate member.

10. An intrauterine device as in claim 1, wherein the intrauterine device is compressible into a collapsed configuration for positioning within a delivery sheath having an inner diameter of no more than 3.9 mm.

11. An intrauterine device as in claim 1, wherein the elongate member has a diameter of between 0.014 inch and 0.015 inch.

12. An intrauterine device as in claim 1, further comprising at least one additional tissue contact member for contacting the uterine wall at a different location.

13. An intrauterine device as in claim 12, wherein the additional tissue contact member comprises at least one fundus contact member coupled with at least one of the two tissue contact members via an additional Nitinol elongate member for contacting a fundus of the uterus.

14. A system for promoting contraception without blocking the fallopian tubes by applying force to a wall of a uterus, the system comprising:
- an elongate, at least partially hollow delivery device having an outer diameter suitable for passing through a cervix;
- an intrauterine device preloaded into the delivery device, wherein the intrauterine device comprises:
- an elongate member formed of Nitinol, having a diameter between 0.010 inch and 0.025 inch, a compressed configuration for residing in the delivery device, a default expanded configuration, and a spring portion disposed approximately at a midpoint between two ends of the elongate member; wherein the elongate member comprises two elongate members that diverge away from one another; and
- two tissue contact members, one of which is disposed at one end of the elongate member and the other of which is disposed at the other end, wherein each tissue contact member comprises a non-porous material and has a surface area of at least 30 mm squared,
- wherein the intrauterine device has a width measured from a tip of one tissue contact member to a tip of the other tissue contact member of at least 40 mm in its expanded configuration outside the uterus.

15. A system as in claim 14, further comprising a substance for delivering to the uterus through the intrauterine device.

16. A system as in claim 15, wherein the substance is selected from the group consisting of hormones, spermicides, copper and therapeutic agents.

17. A system as in claim 14, wherein the delivery device has an inner diameter of no more than 3.9 mm.

\* \* \* \* \*